(12) United States Patent
Yamada et al.

(10) Patent No.: US 7,837,699 B2
(45) Date of Patent: Nov. 23, 2010

(54) ULTRASONIC TREATMENT APPARATUS

(75) Inventors: Norihiro Yamada, Tokyo (JP); Hiroyuki Takahashi, Tokyo (JP); Haruhiko Ueno, Tokyo (JP); Hiroyoshi Watanabe, Aomori (JP); Keita Suzuki, Tokyo (JP); Takeaki Nakamura, Tokyo (JP)

(73) Assignee: Olympus Corporation, Tokyo (JP)

( * ) Notice: Subject to any disclaimer, the term of this patent is extended or adjusted under 35 U.S.C. 154(b) by 372 days.

(21) Appl. No.: 11/485,561

(22) Filed: Jul. 12, 2006

(65) Prior Publication Data

US 2006/0264750 A1    Nov. 23, 2006

Related U.S. Application Data

(63) Continuation of application No. PCT/JP2004/019027, filed on Dec. 20, 2004.

(30) Foreign Application Priority Data

Jan. 13, 2004  (JP) .......................... 2004-005542
Apr. 16, 2004  (JP) .......................... 2004-121424

(51) Int. Cl.
*A61B 17/32* (2006.01)
*A61B 8/14* (2006.01)

(52) U.S. Cl. ...................................... 606/169; 600/459
(58) Field of Classification Search ................. 606/169; 623/1.11; 600/459
See application file for complete search history.

(56) References Cited

U.S. PATENT DOCUMENTS

| 5,162,044 | A | * | 11/1992 | Gahn et al. ................. 604/22 |
| 5,322,055 | A | * | 6/1994 | Davison et al. ............... 601/2 |
| 5,649,935 | A | | 7/1997 | Kremer et al. |
| 6,004,335 | A | * | 12/1999 | Vaitekunas et al. ........... 606/169 |
| 6,056,735 | A | * | 5/2000 | Okada et al. ................... 606/1 |
| 6,165,191 | A | * | 12/2000 | Shibata et al. ............... 606/169 |
| 6,193,709 | B1 | * | 2/2001 | Miyawaki et al. ............... 606/1 |
| 6,231,578 | B1 | | 5/2001 | Rajhansa |
| 6,280,407 | B1 | * | 8/2001 | Manna et al. ................. 604/22 |
| 6,358,264 | B2 | * | 3/2002 | Banko ......................... 606/169 |
| 2002/0002378 | A1 | * | 1/2002 | Messerly ..................... 606/169 |
| 2003/0135136 | A1 | | 7/2003 | Murakami |

FOREIGN PATENT DOCUMENTS

| JP | 05-042156 | 2/1993 |
| JP | 11-056850 | 3/1999 |
| JP | 2000-185052 A | 7/2000 |
| JP | 2003-265496 | 9/2003 |
| WO | WO 98/16156 | 4/1998 |

* cited by examiner

*Primary Examiner*—Anhtuan T Nguyen
*Assistant Examiner*—Jocelin C Tanner
(74) *Attorney, Agent, or Firm*—Scully, Scott, Murphy & Presser, P.C.

(57) ABSTRACT

An ultrasonic treatment apparatus includes a sheath having an opening at a distal end thereof; an ultrasonic transducer provided at a distal portion of the sheath and generating ultrasonic vibration; an ultrasonic transmission member connected to the ultrasonic transducer at a proximal end thereof, transmitting the ultrasonic vibration, and provided with a treatment part at a distal end thereof; a gripper moving to the treatment part and grasping the part to be treated between the gripper and the treatment part; a link member connected to the gripper and provided on a side of the ultrasonic transmission member; a manipulator part connected to a proximal end part of the link member to open and close the gripper; and a rigid member which the ultrasonic transducer is inserted into and secured to.

10 Claims, 24 Drawing Sheets

US 7,837,699 B2

ULTRASONIC TREATMENT APPARATUS

CROSS-REFERENCE TO RELATED APPLICATIONS

This application is a continuation of PCT international application Ser. No. PCT/JP2004/019027 filed Dec. 20, 2004 which designates the United States, incorporated herein by reference, and which claims the benefit of priority from Japanese Patent Applications No. 2004-005542 filed Jan. 13, 2004; and No. 2004-121424 filed Apr. 16, 2004, incorporated herein by reference.

BACKGROUND OF THE INVENTION

1. Field of the Invention

The present invention relates to an ultrasonic treatment apparatus used for, for example, observing a part to be treated inside body cavity as well as cutting and coagulating the part to be treated.

2. Description of the Related Art

A conventional ultrasonic treatment apparatus used for an endoscope is, for example, configured to insert a flexible wire having a loop at a distal end part thereof into a channel, as disclosed in U.S. Pat. No. 6,231,578. Then, an operator manipulates the ultrasonic treatment apparatus to perform treatments such as cutting body tissue on a part to be treated inside a patient body, while transmitting ultrasonic vibration produced by an ultrasonic transducer housed in a manipulator unit to the flexible wire.

Another conventional ultrasonic treatment apparatus is, for example, configured to combine a small ultrasonic transducer and a forceps capable of being inserted into a channel of an endoscope, as disclosed in U.S. Pat. No. 5,649,935. This ultrasonic transducer includes a piezoelectric element that transduces electric signals into mechanical vibration, a horn that is a squeeze part to amplify the vibration, and a distal end part thereof that transmits ultrasonic vibration to a part to be treated or to a member used for treatment.

SUMMARY OF THE INVENTION

An ultrasonic treatment apparatus according to one aspect of the present invention includes a sheath that has an opening at a distal end thereof; an ultrasonic transducer that is provided at a distal portion of the sheath, and generates ultrasonic vibration; an ultrasonic transmission member that is connected to the ultrasonic transducer at a proximal end thereof, transmits the ultrasonic vibration, and is provided with a treatment part at a distal end thereof, the treatment part treating a part of a patient to be treated; a gripper that moves to the treatment part, and grasps the part to be treated between the gripper and the treatment part; a link member that is connected to the gripper, and provided on a side of the ultrasonic transmission member; a manipulator part that is connected to a proximal end part of the link member to open and close the gripper; and a rigid member which the ultrasonic transducer is inserted into and secured to.

An ultrasonic treatment apparatus according to another aspect of the present invention includes a sheath that has an opening at distal end thereof; an ultrasonic transducer that is provided at a distal portion of the sheath, and generates ultrasonic vibration; an ultrasonic transmission member that is connected to the ultrasonic transducer at a proximal end thereof, transmits the ultrasonic vibration, and is provided with a treatment part at a distal end thereof, the treatment part treating a part of a patient to be treated; a gripper that moves to the treatment part, and grasps the part to be treated between the gripper and the treatment part; a link member that is connected to the gripper, and provided on a front side of the ultrasonic transmission member; a manipulator part that is connected to a proximal end part of the link member to open and close the gripper; and a rigid member which the ultrasonic transducer is inserted into and secured to.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of an ultrasonic treatment apparatus according to the present invention are explained in detail below with reference to the accompanying drawings. The present invention is not limited to the embodiments.

Figure 1:
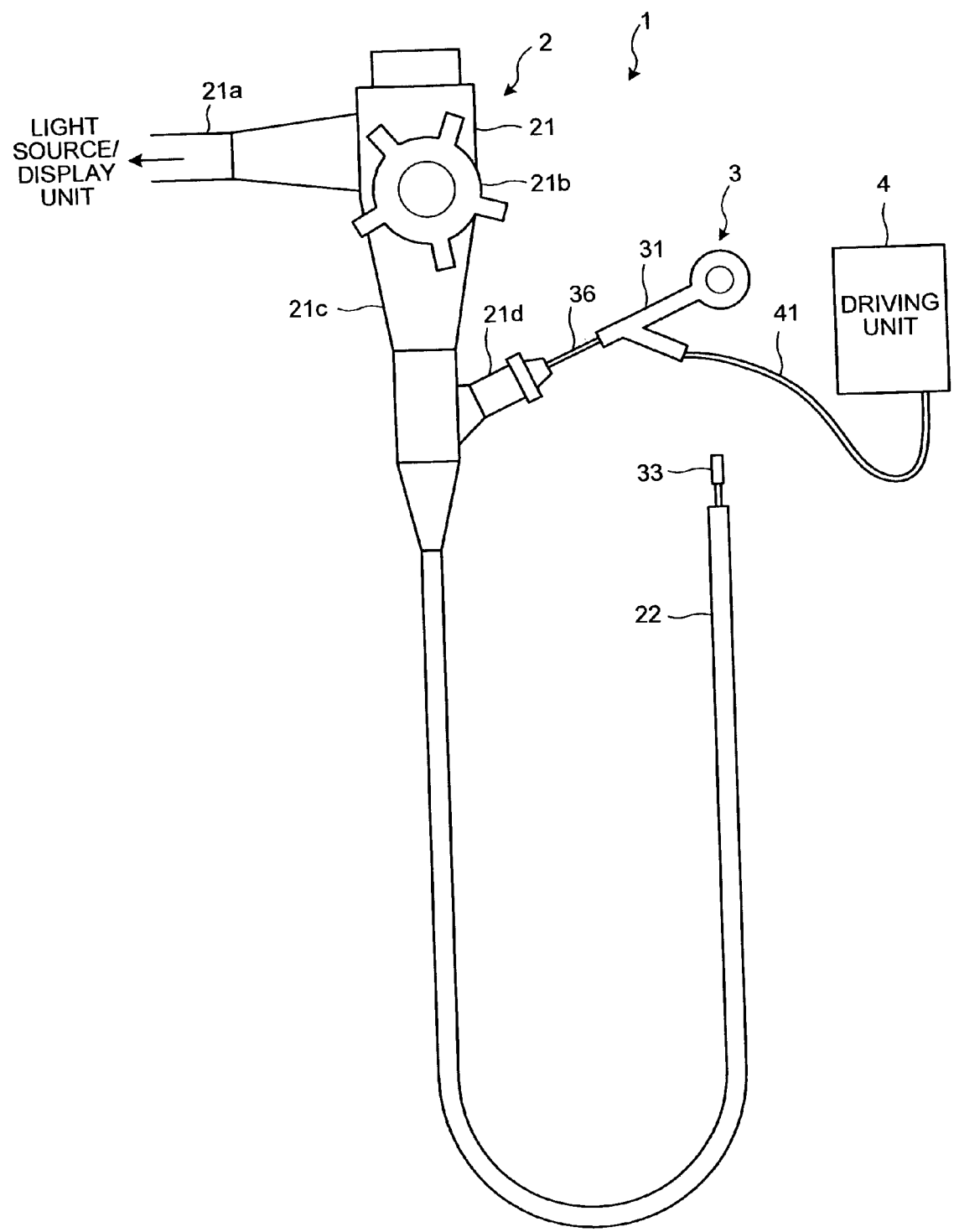
FIG. 1 is a schematic diagram showing one example of a configuration of an ultrasonic treatment apparatus used for an endoscope device, according to the present invention.

FIG. 1 is a schematic diagram showing one of the examples of a configuration of an ultrasonic treatment apparatus used for an endoscope device 1, according to the present invention. The endoscope device 1 includes a video scope 2 connected to a light source and a display unit not shown, an ultrasonic treatment apparatus 3, and a driving unit 4 that supplies current to the ultrasonic treatment apparatus 3. The ultrasonic treatment apparatus 3 and the driving unit 4 are connected by a signal cable 41.

The video scope 2 is provided with an elongated cylinder-shaped insert part 22 that is to be inserted into a patient body and a scope manipulator part 21 that is provided at a proximal end side of the insert part 22. A flexible universal code 21a connecting the scope manipulator part 21 to the light source and the display unit is connected to a side face of the scope manipulator part 21. Further, a protruding bending manipulator knob 21b used to manipulate bending of a distal end of the insert part 22 is provided on a side face of the scope manipulator part 21 in which a location of the side face corresponding to the scope manipulator part 21 differs from a location of the side face corresponding to the universal code 21a. Although a protruding aspiration opening metal fitting and a protruding water supply opening metal fitting are provided at side faces of the manipulator part 21 when an aspiration channel and a water supply channel are provided in the video scope 2, the configuration thereof is not shown since it is not necessarily required in the present invention.

Further, a grasp part 21c is provided in the scope manipulator part 21 to hold and stabilize the video scope 2 by when grasped by an operator. A protruding forceps insert opening 21d used for inserting a forceps, which is the ultrasonic treatment apparatus 3 according to the present invention, is provided at an attaching side to which the insert part 22 is attached. FIG. 1 shows a condition that the ultrasonic treatment apparatus 3 is inserted into the forceps insert opening 21d and a manipulator unit 31 that manipulates the ultrasonic treatment apparatus 3 through a flexible sheath 36 is protruded from the forceps insert opening 21d.

Figure 2:
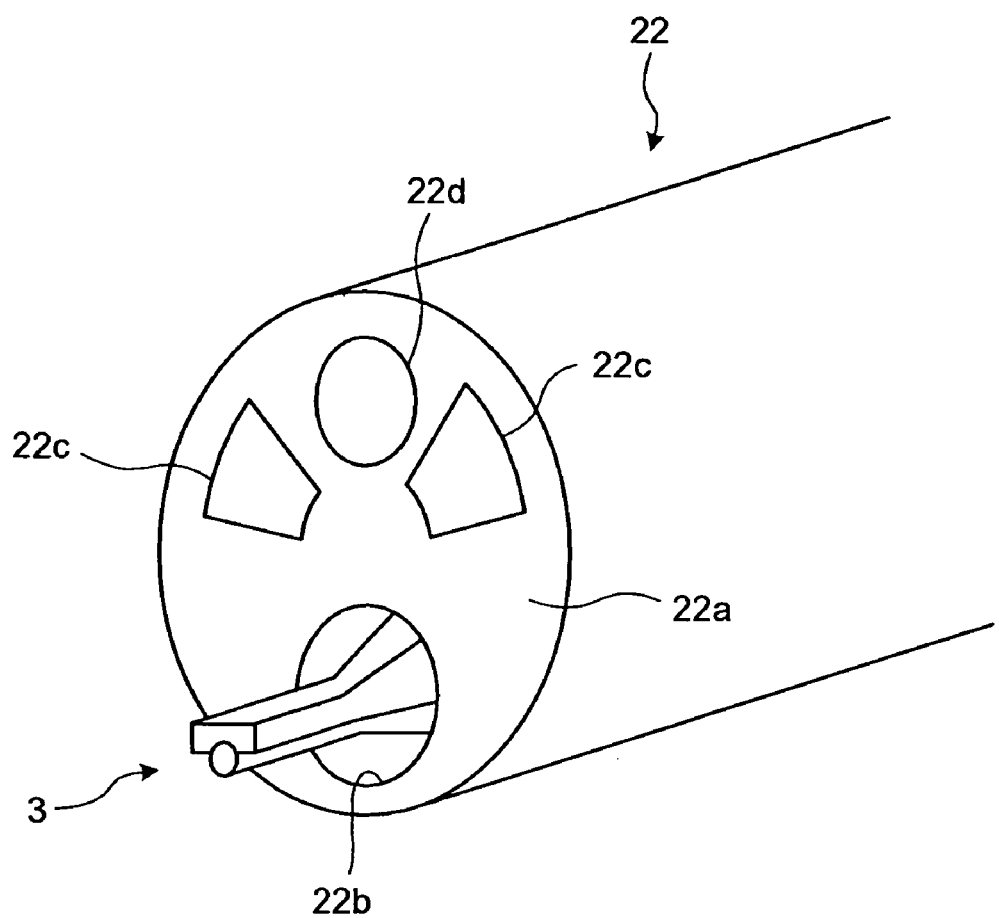
FIG. 2 is a perspective view showing the example of a configuration at a distal end part of an insert part shown in FIG. 1.

The insert part 22 to be inserted into the patient body is provided with components such as a rigid distal end part 22a provided at a distal end of the insert part 22, a bending part not shown that bends due to manipulation of the scope manipulator part 21 not shown, and a flexible duct that has flexibility, and the components are configured to be aligned. FIG. 2 is a perspective view showing one of the examples of a configuration at the distal end part of the insert part shown in FIG. 1. A channel 22b is formed at the distal end part 22a of the insert part 22, and the ultrasonic treatment apparatus 3 is protrudably installed inside the channel 22b. Further, the distal end part 22a of the insert part 22 is provided with one observation window 22d that is configured by a observation system lens, and with two illumination windows 22c that are secured to the distal end and configured by illuminating system lenses.

A Charge-Coupled Device (CCD) not shown, which is a solid-state image sensor, is attached to the inmost of the observation window 22d, and a variety of circuit substrates are secured to a lead provided on back of the CCD. Furthermore, one end of a signal cable that transmits image signals from the circuit substrate is connected to a proximal end of the circuit substrate, and other end of the signal cable is connected to the display unit through the universal code 21a. Further, one end of an optical guide fiber provided in the insert part 22 is provided at the illumination windows 22c, and other end thereof is connected to the light source through the universal code 21a. Illumination light emitted from the light source is emitted through the optical guide fiber, and the illumination light is emitted from the illumination windows 22c of the distal end part 22a to outside, such as to a part to be treated inside body cavity. The observation system lens is configured by, for example, a combination of two lenses (not shown), and reflecting light from the part to be treated inside the body cavity is acquired by the CCD. Then, the image data from the CCD is transmitted as video signals to the signal cable after being subjected to image processing at the circuit substrate. The transmitted video signals are sent through the signal cable to the display unit arranged at the other end of the signal cable, and the image of the part to be treated is displayed. Hence, an operator can observe the part to be treated.

Figure 3:
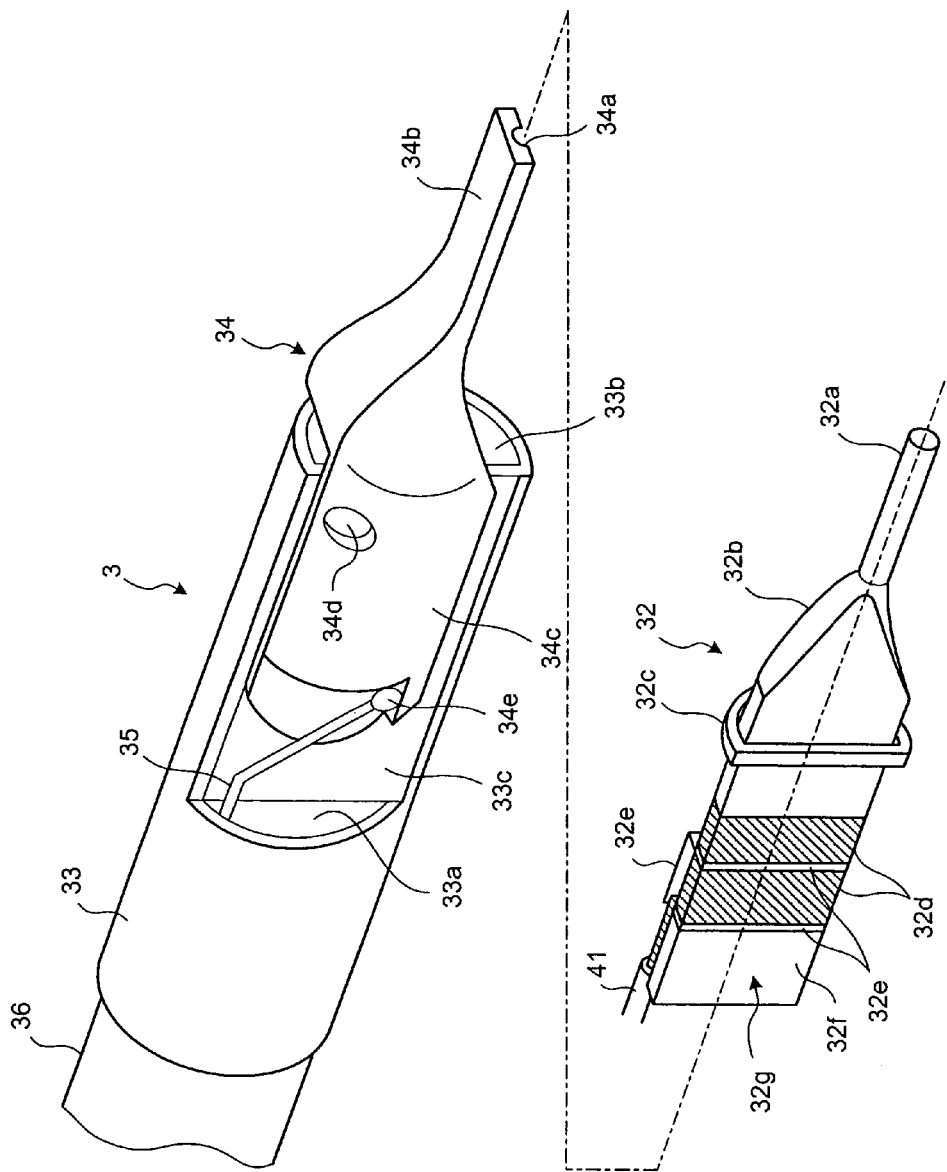
FIG. 3 is a perspective view showing a configuration of a first embodiment of a distal end section of the ultrasonic treatment apparatus according to the present invention.
Figure 4:
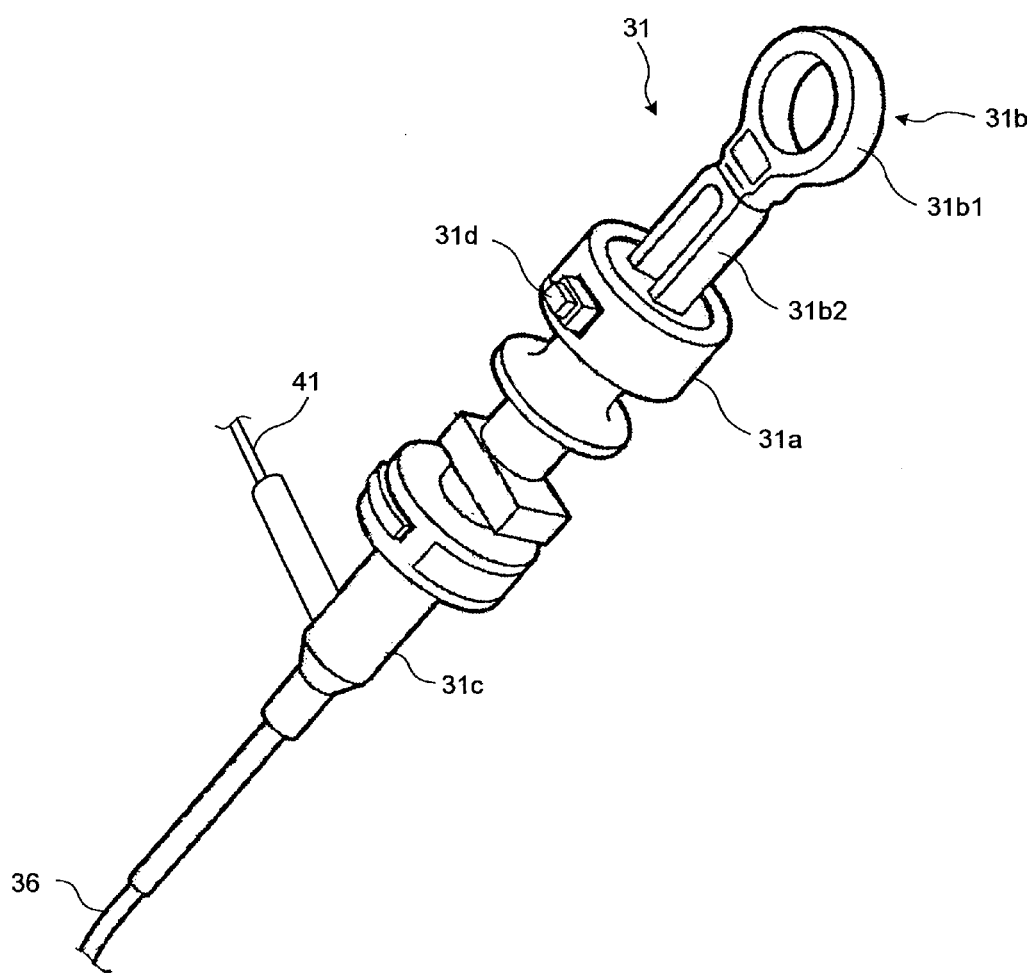
FIG. 4 is a perspective view showing a configuration of one of the examples of a manipulator unit of the ultrasonic treatment apparatus shown in FIG. 1.
Figure 5:
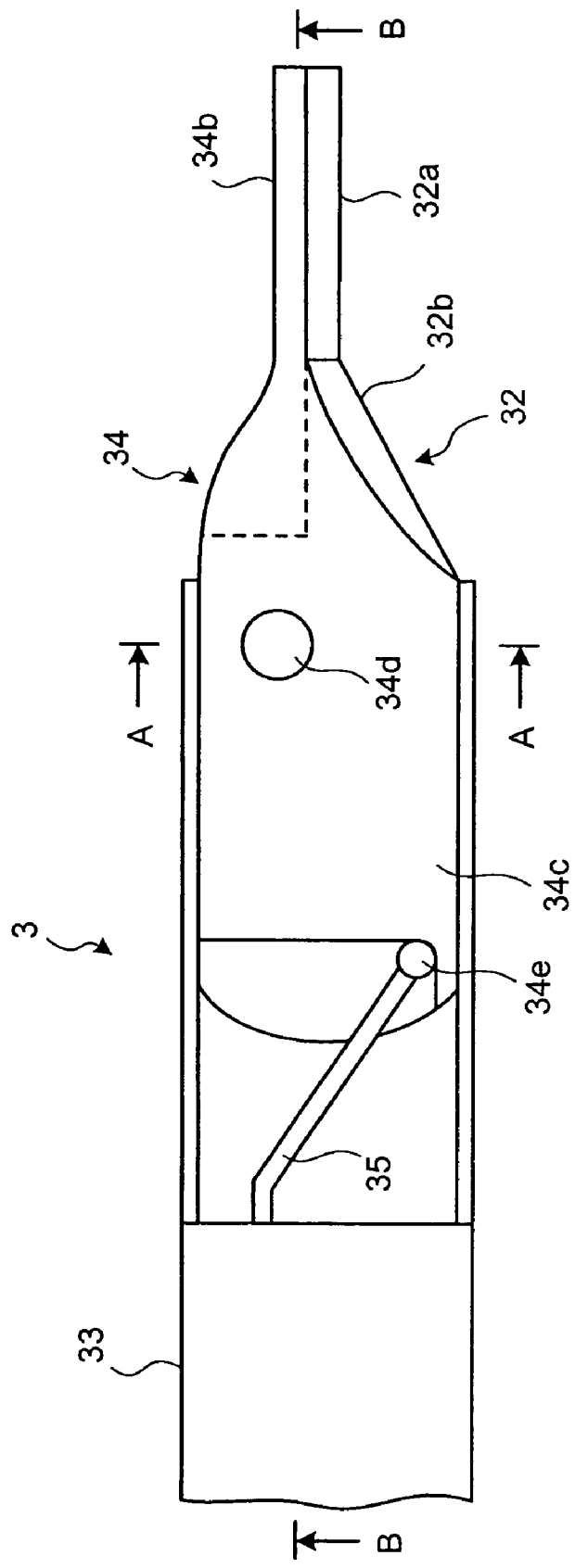
FIG. 5 is a side view showing a side face of the ultrasonic treatment apparatus when the distal end section of the ultrasonic treatment apparatus is closed.
Figure 6:
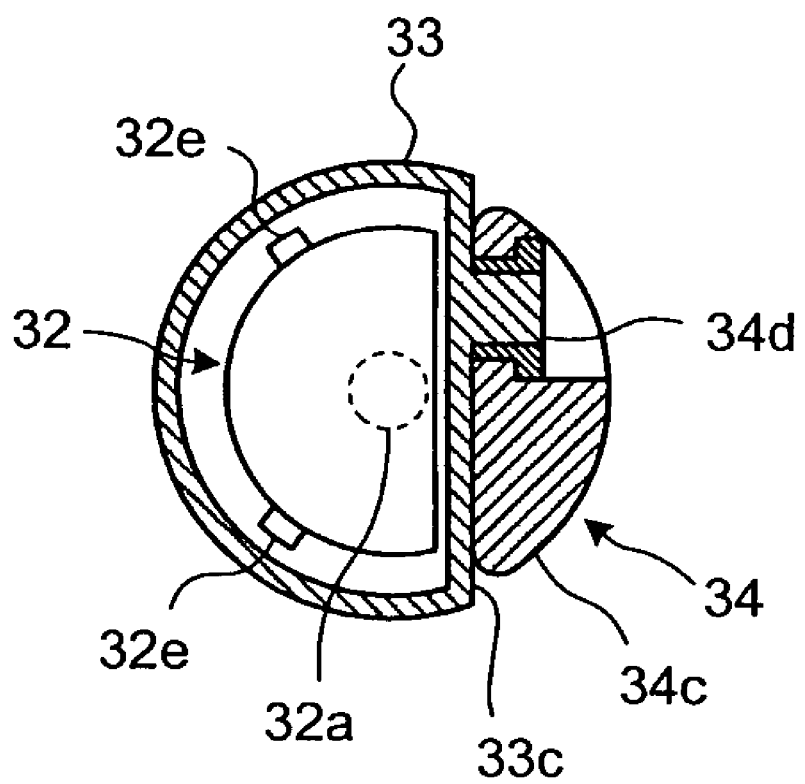
FIG. 6 is an A-A cross-sectional view of FIG. 5.
Figure 7:
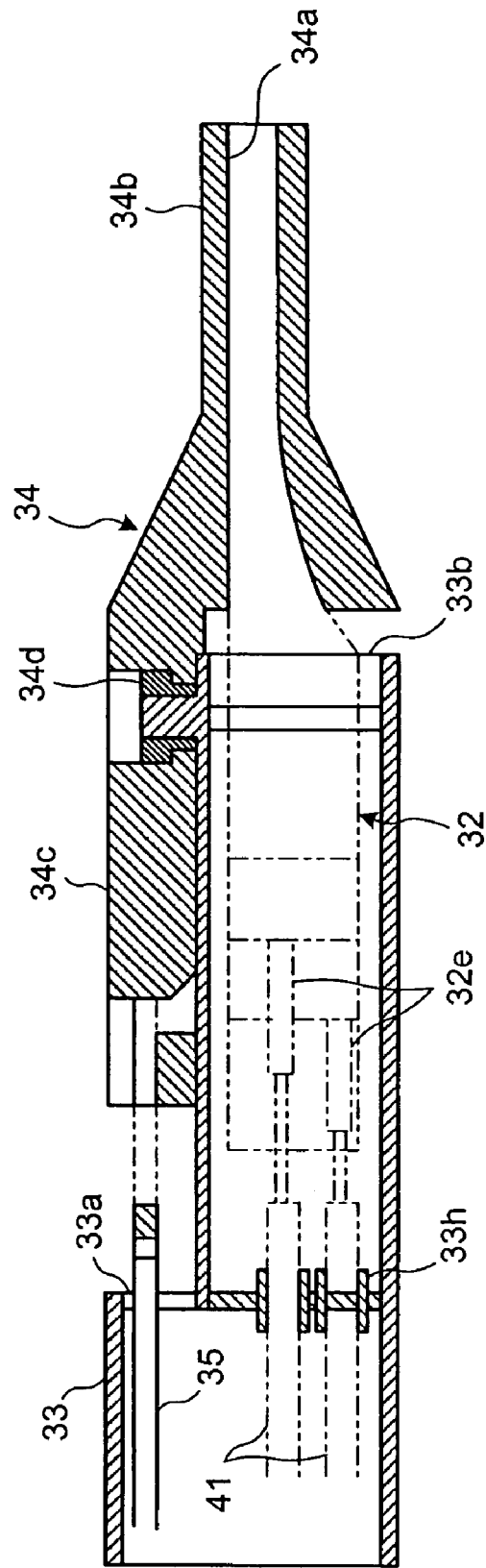
FIG. 7 is a B-B cross-sectional view of FIG. 5.
Figure 8:
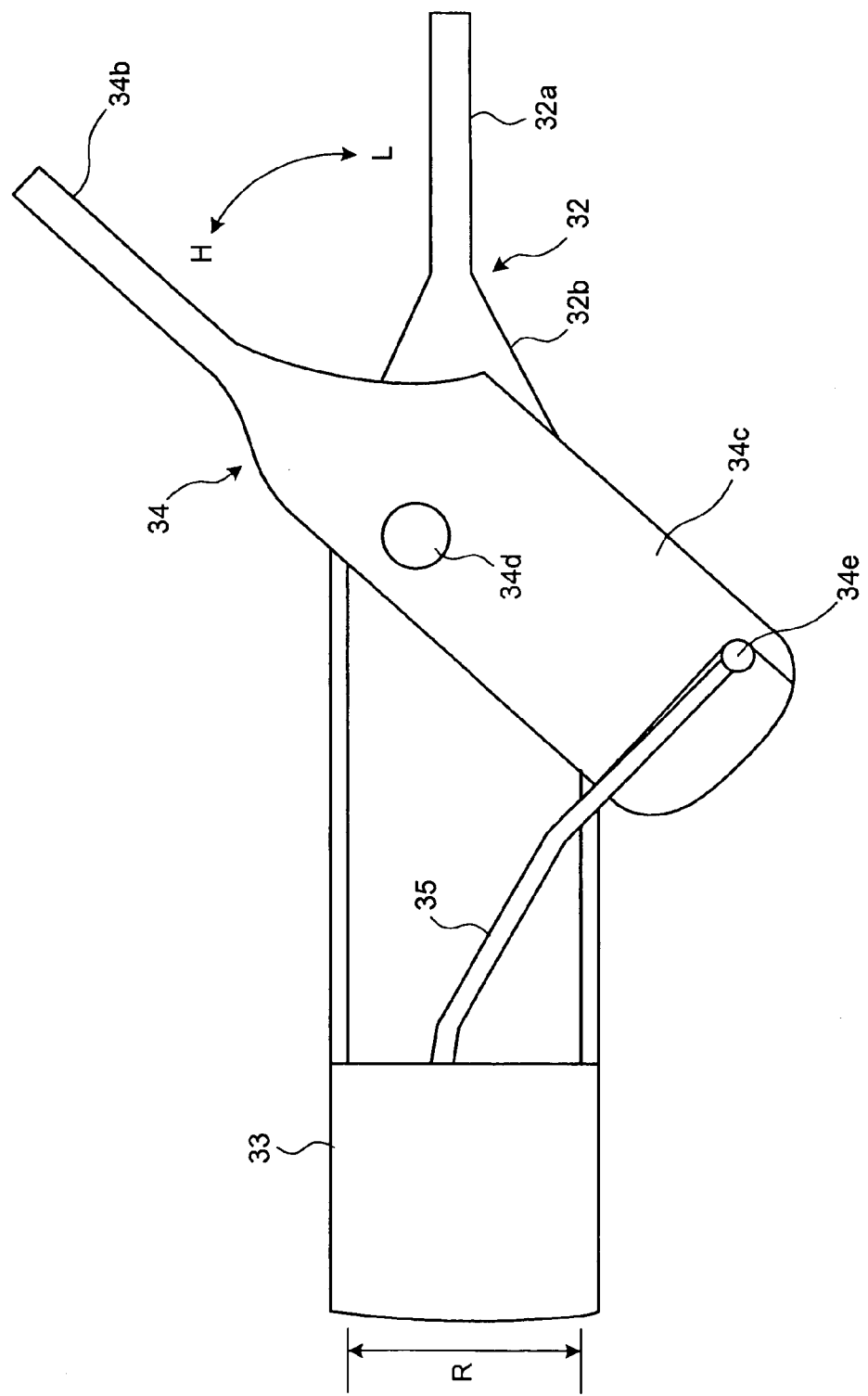
FIG. 8 is a side view showing the side face of the ultrasonic treatment apparatus when the distal end section of the ultrasonic treatment apparatus is opened.

FIG. 3 is a perspective view showing a configuration of a first embodiment of a distal end section of the ultrasonic treatment apparatus according to the present invention. FIG. 4 is a perspective view showing a configuration of one of the examples of the manipulator unit of the ultrasonic treatment apparatus shown in FIG. 1. FIG. 5 is a side view showing a side face of the ultrasonic treatment apparatus when the distal end section of the ultrasonic treatment apparatus is closed. FIG. 6 is an A-A cross-sectional view of FIG. 5, and FIG. 7 is a B-B cross-sectional view of FIG. 5. FIG. 8 is a side view showing the side face of the ultrasonic treatment apparatus when the distal end section of the ultrasonic treatment apparatus is opened. In FIGS. 1 and 3, the ultrasonic treatment apparatus 3 is configured by the manipulator unit 31, an ultrasonic transducer 32 provided at the distal end section of the ultrasonic treatment apparatus 3 to cause ultrasonic vibration, a cylinder-shaped rigid member 33 that secures the ultrasonic transducer 32, a gripper 34 that grasps the part to be treated, a manipulator wire 35 that configures the manipulator unit 31 in conjunction with the manipulator unit, and the flexible sheath 36 in which one end thereof is connected to the manipulator unit 31 and other end is connected to the rigid member 33 when the manipulator wire 35 is inserted through the flexible sheath 36.

As shown in FIG. 4, the manipulator unit 31 is provided with a substantially cylinder-shaped manipulator unit main body 31a, a ring part 31b provided at one end of the manipulator unit main body 31a to advance and retreat the manipulator wire 35, two ways joint 31c provided at the other end of the manipulator unit main body 31a to which each of the manipulator wire 35 and the signal cable 41 extending from the driving unit 4 is connected, and a switch 31d that is provided at a side face of the manipulator unit main body 31a to control running and stopping of electric signals from the driving unit 4. The signal cable 41 is bent inside the joint 31c, and the signal cable 41 is inserted into the flexible sheath 36 with the manipulator wire 35 and connected to the ultrasonic transducer 32 provided at the distal end of the insert part 22. Consequently, the electric signals can be supplied to the ultrasonic transducer 32.

The ring part 31b is configured by a hollow ring 31b1 and an insert member 31b2 in which one end thereof is connected to the ring 31b1 and other end thereof is loosely inserted into the manipulator part main body 31a and connected to the manipulator wire 35. One end of the manipulator wire 35 inside the flexible sheath 36 is connected to the insert member 31b2 and other end thereof is connected to a proximal end part of the gripper 34. The insert member 31b2 is inserted into the manipulator unit main body 31a when an operator inserts his/her finger into the ring 31b1 of the ring part 31b and pushes the ring part 31b toward the manipulator unit main body 31a. Further, the insert member 31b2 protrudes from inside the manipulator unit main body 31a when the ring part 31b is shifted away from the manipulator unit main body 31a. Consequently, the manipulator wire 35 advances and retreats inside the flexible sheath 36, and the gripper 34 can be opened and closed. Further, the flexible sheath 36 is inserted into the video scope 2 when the manipulator unit main body 31a is pushed toward the forceps insert opening 21d, and the flexible sheath 36 protrudes from inside the video scope 2 to outside thereof when the manipulator unit main body 31a is shifted away from the forceps insert opening 21d. Consequently, the distal end section of the ultrasonic treatment apparatus 3 protrudes from the distal end of the insert part 22 or the distal end section shifts toward the channel to be housed inside the channel.

As shown in the perspective view of FIG. 3, the ultrasonic transducer 32 is provided with an axially elongated cylinder-shaped distal end treatment part 32a, a horn 32b that transmits ultrasonic vibration to the distal end treatment part 32a, a flange 32c that secures the ultrasonic transducer 32 to the rigid member 33, a piezoelectric element 32d that generates ultrasonic vibration, two electrodes 32e that supply electric signals from the signal cable 41 in which each of the electrodes 32e is connected to the piezoelectric element 32d, and a base 32f.

The ultrasonic transducer 32 has substantial semi-cylinder shape having an axially provided side plane 32g, and a cross section of the ultrasonic transducer 32 is D-shaped in radial direction as shown in A-A cross-sectional view of FIG. 6. Further, the flange 32c has hollow D shape to coincide with the shape of the ultrasonic transducer 32 (see FIG. 3). The flange 32c is provided on periphery of the ultrasonic transducer 32 as well as at an equilibrium point of the vibration. Further, the flange 32c is secured to an end part of the transducer insert hole 33b of the rigid member 33 having a shape identical to the shape of the flange 32c. Oblique lines of the cross section of the ultrasonic transducer 32 is omitted in FIG. 6 to make recognition of the shape easy, and the ultrasonic transducer 32 is shown by two points chained line in FIG. 7.

The electric signals from the driving unit 4 described above is supplied to the piezoelectric element 32d through the signal cable 41, and the piezoelectric element 32d generates ultrasonic vibration by receiving the electric signals. Amplitude of the caused ultrasonic vibration is amplified due to the vibration transmitting through the squeeze-shaped horn 32b, and the ultrasonic vibration is transmitted to the distal end treatment part 32a.

The rigid member 33 is, for example, formed by a hollow cylinder-shaped metal member as shown in FIGS. 3 and 7. One end of the rigid member 33 is connected to the flexible sheath 36, and a manipulator wire insert hole 33a and the transducer insert hole 33b is provided at the other end thereof. The manipulator wire 35 penetrates the manipulator wire insert hole 33a, and one end of the manipulator wire 35 is engaged to the gripper 34 by a manipulator pin 34e. The transducer insert hole 33b is formed to have an axially longer hole compared to the manipulator wire insert hole 33a, and D shape similar to the shape of the ultrasonic transducer 32. Further, the ultrasonic transducer 32 is inserted into and secured to the transducer insert hole 33b. The signal cable 41 connected to the electrodes 32e penetrates a diaphragm 33h, and the signal cable 41 is connected to the outer driving unit 4 with the manipulator wire 35 through the flexible sheath 36. Here, outer diameter of a cylinder section of the rigid member 33 is set to be smaller than inner diameter of the channel 22b in order to allow the rigid member 33 to be housed inside the channel 22b and to be protruded from the channel 22b.

As shown in FIG. 3, the gripper 34 includes a link body part 34c and a box-like grasp member 34b having an axially elongated groove part 34a at base therein. In the present embodiment, the groove part 34a of the grasp member 34b is formed to contact the distal end treatment part 32a of the ultrasonic transducer 32 and engages thereto when the grasp member 34b is closed, as shown in FIG. 5.

As shown in FIG. 6, the link body part 34c has a D-shaped section so that a complete circle is formed with the rigid member 33 as being a circle missing a piece. The link body part 34c is provided with a supporting pin 34d that rotatably holds the link body part 34c so that the link body part 34c extends along a sidewall 33c of the rigid member 33 provided on the side of the ultrasonic transducer 32. The link body part 34c is also provided with a manipulator pin 34e in a way so that one end of the manipulator wire 35 engages to the link body part 34c at a sidewall 33c of the rigid member 33 provided at the side of the ultrasonic transducer 32.

A horizontal diameter combining a diameter of the rigid member 33 and a diameter of the link body part 34c shown in FIG. 6 is substantially equal to the outer diameter of the flexible sheath 36 when the grasp member 34b is closed. Consequently, the ultrasonic treatment apparatus can be housed inside the channel 22b and the ultrasonic treatment apparatus can protrude from the channel 22b. Further, the gripper 34 rotates with respect to the supporting pin 34d when the grasp member 34b is opened as shown in FIG. 8; therefore, the stroke of the gripper 34 becomes larger than the inner diameter R of the rigid member 33.

Next, a situation when the body tissue such as polyps inside the patient body is treated, is explained using side views of FIGS. 5 and 8. First, the insert part 22 of the video scope 2 is inserted into the patient body. The body tissue, which is the part to be treated, is recognized by observing inside the patient body through the observation window 22d while illuminating the region by emitted illumination light from the illumination windows 22c. When the distal end of the insert part 22 reaches near the body tissue needing to be treated, the ultrasonic treatment apparatus 3 is inserted into the channel 22*b* from the forceps insert opening 21*d* after specifying the part to be treated while having the gripper 34 closed. In the present invention, the insert part 22 of the video scope 2 can be inserted into the patient body when the distal end of the ultrasonic treatment apparatus 3 is housed in the channel 22*b* as shown in FIG. 2. Next, the flexible sheath 36 is shifted inside the insert part 22 toward the distal end direction by the operator pushing the manipulator unit main body 31*a* of the manipulator unit 31 toward the video scope 2. Consequently, the distal end of the ultrasonic treatment apparatus 3 protrudes into the patient body.

Next, when the operator inserts one's finger into the ring 31*b*1 of the ring part 31*b* and pushes the ring part 31*b* into the manipulator unit main body 31*a*, the flexible sheath 36 shifts toward the distal end direction thereof since the manipulator wire 35 is linked up with the ring part 31*b*. Then, the gripper 34 opens when the grasp member 34*b* of the gripper 34 is rotated toward H direction of an arrow shown in FIG. 8 with respect to the supporting pin 34*d* that is a fulcrum. Next, the insert part 22 is manipulated to locate the body tissue in between the grasp member 34*b* of the gripper 34 and the distal end treatment part 32*a* of the ultrasonic transducer 32. Then, the grasp member 34*b* is rotated toward the L direction of an arrow with respect to the supporting pin 34*d* that is the fulcrum, when the operator shifts the ring part 31*b* away from the manipulator unit main body 31*a*. Consequently, spacing between the distal end treatment part 32*a* and the grasp member 34*b* narrows, and the body tissue is grasped.

Next, ultrasonic vibration due to the ultrasonic transducer 32 is caused when a switch 31*d* of the manipulator unit 31 is turned on to supply the electric signals from the driving unit to the ultrasonic transducer 32. The amplitude of the ultrasonic vibration is amplified by the horn 32*b*, and the ultrasonic vibration is transmitted to the distal end treatment part 32*a*. When the vibration of the distal end treatment part 32*a* is initiated, the body tissue contacting the distal end treatment unit 32*a* is cut by the ultrasonic vibration as well as the part to be treated is coagulated by frictional heat.

In the present embodiment, the horn of the ultrasonic transducer, the piezoelectric element, and the base have substantially semi-cylindrical shape having axially provided side plane, and the rigid member has cylindrical shape with D-shaped partially circular cross section, in order to obtain a space for providing the link body part of the gripper on the side of the ultrasonic transducer. Consequently, the link body used to open and close the gripper is effectively housed inside the sheath. Here, the grasping of the part to be treated inside the patient body is allowed by placing the part to be treated in between the gripper and the treatment part. Therefore, overall size of the ultrasonic treatment apparatus can be downsized as well as large stroke for opening and closing the gripper can be obtained, and the surgical operation of the body tissue inside the patient body can be easily performed by ultrasonic vibration.

Figure 9:
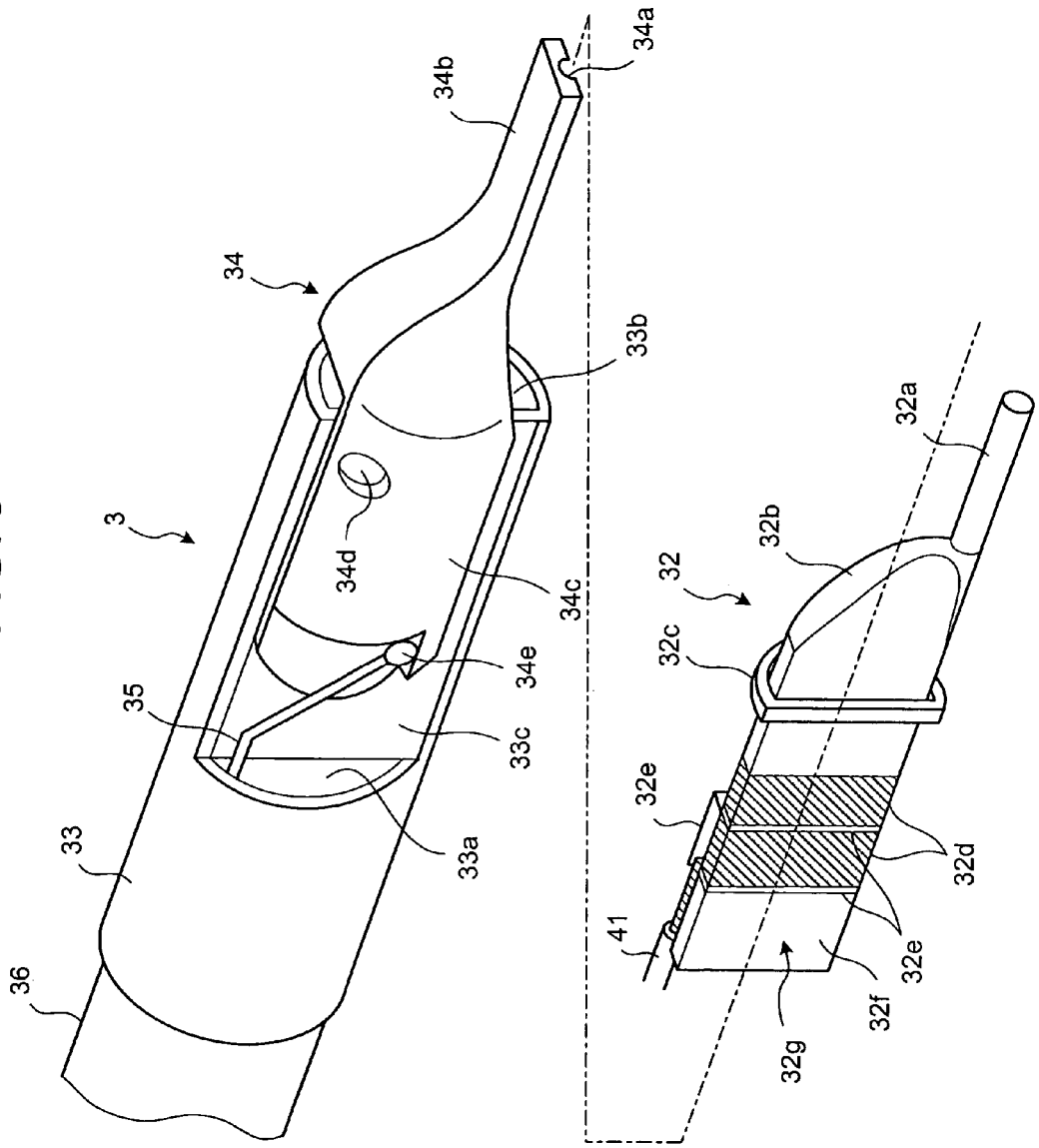
FIG. 9 is a perspective view showing a configuration of a modification of the first embodiment of the distal end section of the ultrasonic treatment apparatus shown in FIG. 3.

FIG. 9 is a perspective view showing a configuration of a modification of the first embodiment of the distal end section of the ultrasonic treatment apparatus shown in FIG. 3. In the following drawings, same symbols and numbers are assigned for components that are similar to the components shown in FIGS. 3 to 8, for convenience of the explanation. The configuration in FIG. 9 differs from the configuration in FIG. 3 only by the configurations in which the distal end treatment part 32*a* of the ultrasonic transducer 32 is provided in eccentric position with respect to a central axis of the flexible sheath 32 and the distal end treatment part 32*a* is arranged at lower part of the ultrasonic transducer 32. Correspondingly, the grasp member 34*b* of the gripper 34 is in eccentric position with respect to the central axis of the flexible sheath 36.

The distal end treatment part 32*a* and the grasp member 34*b* are arranged so that the groove part 34*a* of the grasp member 34*b* contacts the distal end treatment part 32*a* of the ultrasonic transducer 32 and engages thereto, when the distal end treatment part 32*a* is closed. While shifting the manipulator wire for the same amount in the modification and the first embodiment, larger stroke of the opening and closing of the gripper 34 can be obtained in the modification compared to the stroke in the first embodiment because the grasp member 34*b* is provided downwards with respect to the center of the flexible sheath. Consequently, the ultrasonic treatment apparatus according to the present invention can be used for treating large body tissue such as polyps inside the patient.

As described above, the horn, the piezoelectric element, and the base of the ultrasonic transducer have the substantial semi-cylindrical shape on the axially provided side plane in the present modification. Further, the rigid member has a cylindrical shape with a D-shaped partially circular section, and the distal end treatment part of the ultrasonic transducer is provided off-centered below the central axis of the inner periphery of the flexible sheath. Consequently, the link body that opens and closes the gripper can be effectively housed inside the sheath, and larger stroke for opening and closing the gripper is obtained. Therefore, treatment of the body tissue inside the patient can be more easily performed by ultrasonic vibration.

Figure 10:
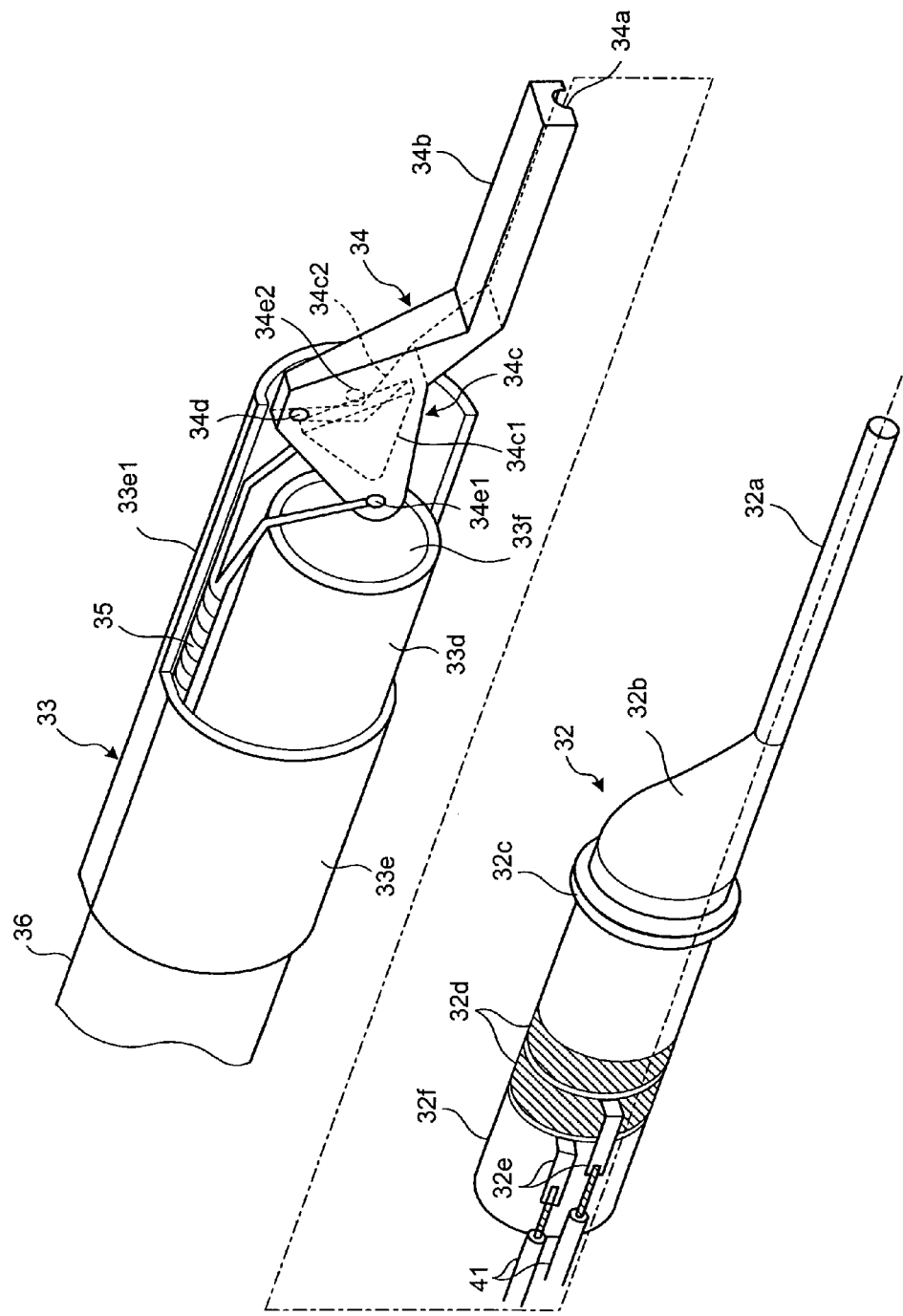
FIG. 10 is a perspective view showing a configuration of a distal end section of an ultrasonic treatment apparatus according to a second embodiment of the present invention.
Figure 11:
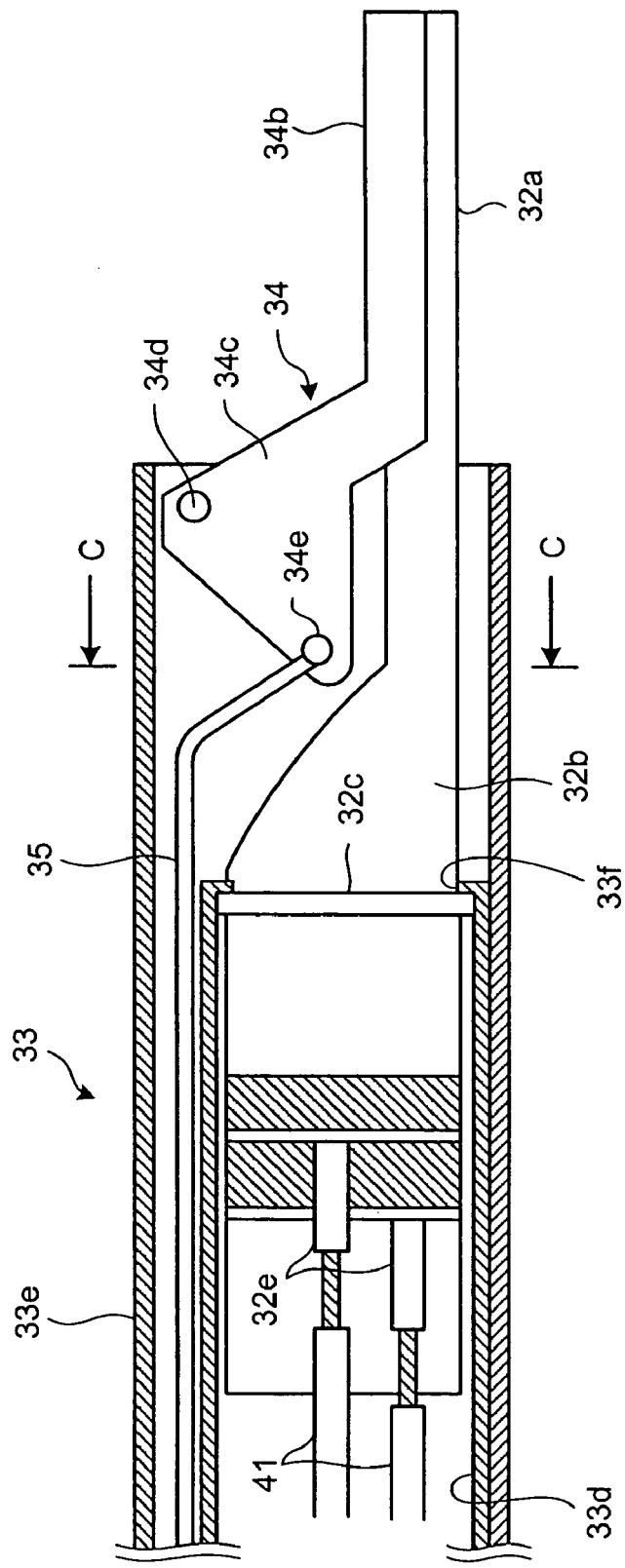
FIG. 11 is a cross-sectional side view of the distal end section of the ultrasonic treatment apparatus in which only a transducer cover and an outer tube are cut, when the distal end section of the ultrasonic treatment apparatus shown in FIG. 10 is closed.
Figure 12:
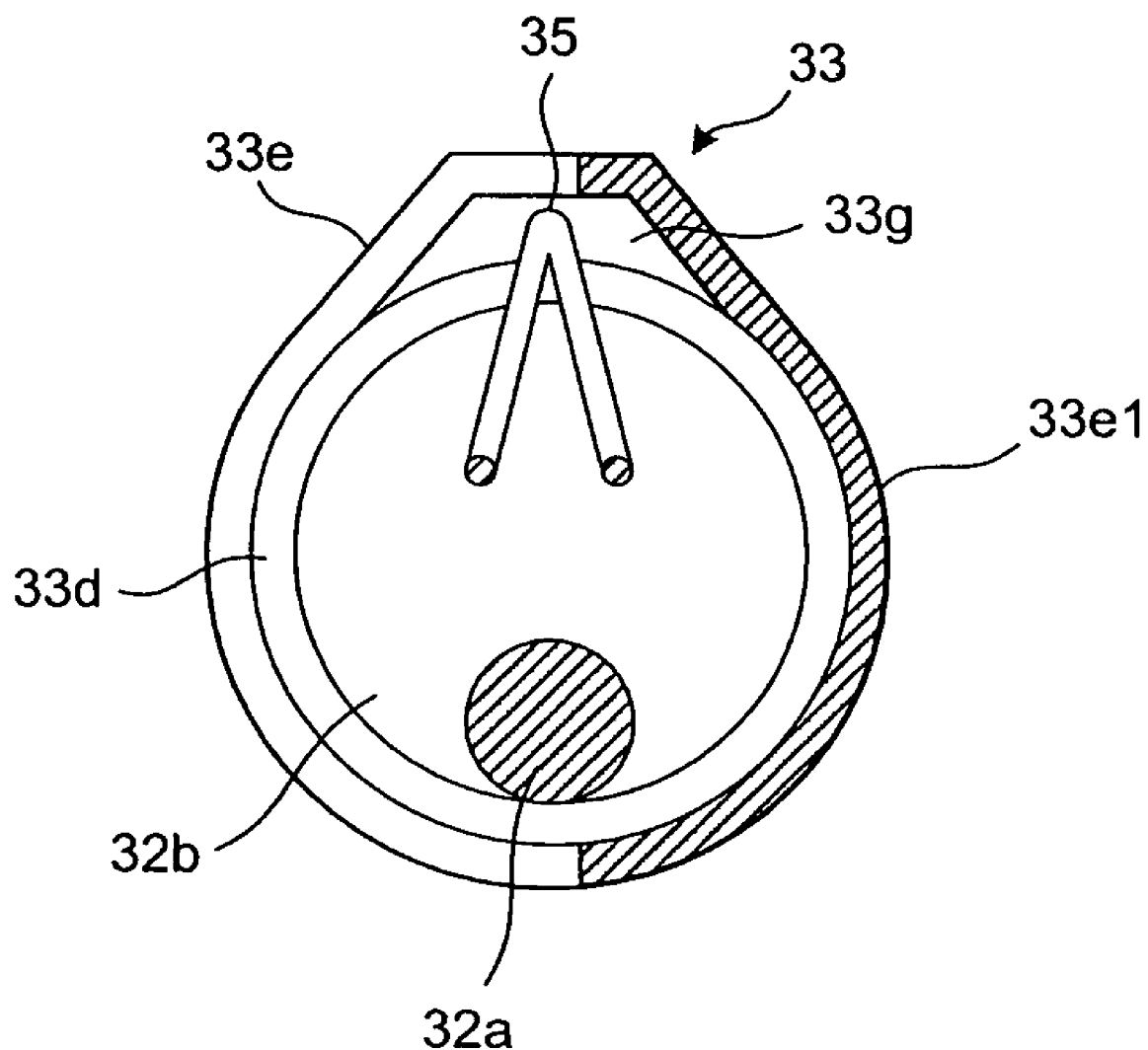
FIG. 12 is a C-C cross-sectional view of FIG. 11.
Figure 13:
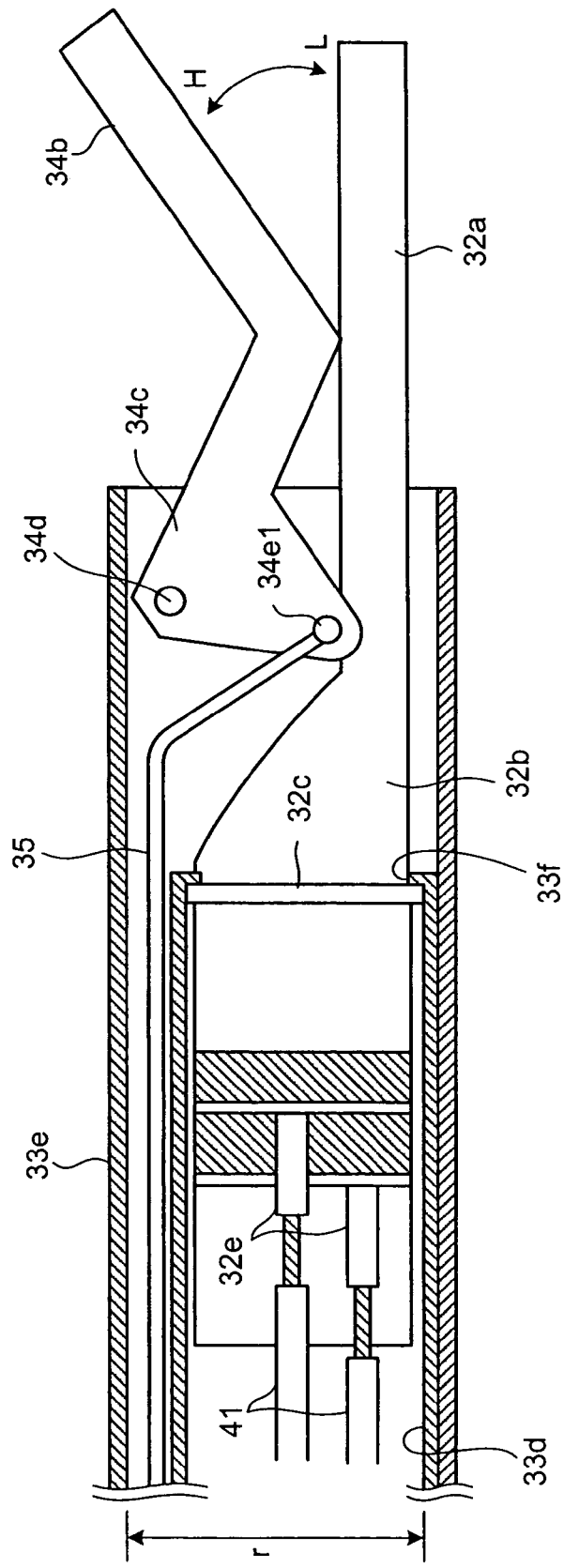
FIG. 13 is a cross-sectional side view of the distal end section of the ultrasonic treatment apparatus in which only the transducer cover and the outer tube are cut, when the distal end section of the ultrasonic treatment apparatus shown in FIG. 10 is opened.

FIG. 10 is a perspective view showing a configuration of the distal end section of the ultrasonic treatment apparatus according to a second embodiment of the present invention. FIG. 11 is a cross-sectional side view of the distal end section of the ultrasonic treatment apparatus in which only a transducer cover and an outer tube are cut, when the distal end section of the ultrasonic treatment apparatus shown in FIG. 10 is closed. FIG. 12 is a C-C cross-sectional view of FIG. 11. FIG. 13 is a cross-sectional side view of the distal end section of the ultrasonic treatment apparatus in which only the transducer cover and the outer tube are cut, when the distal end section of the ultrasonic treatment apparatus shown in FIG. 10 is opened. In the perspective view of FIG. 10, the ultrasonic transducer 32 is provided with the distal end treatment part 32*a*, the horn 32*b*, the flange 32*c*, the piezoelectric element 32*d*, the electrode 32*e*, and the base 32*f*, as similar to the first embodiment.

In the ultrasonic transducer 32, the distal end treatment part 32*a* is off-centered downwards with respect to the central axis of the flexible sheath 36, and arranged at lower part of the ultrasonic transducer 32. Correspondingly, the horn 32*b* has downwards squeezing shape toward the lower part of the ultrasonic transducer 32. The piezoelectric element 32*d*, the base 32*f*, and a portion of the horn 32*b* have cylindrical shape. Further, the flange 32*c* has hollow circular ring shape in order to coincide with the shape of the ultrasonic transducer 32. The flange 32*c* is provided around the periphery of the ultrasonic transducer 32 as well as provided at the equilibrium point of the vibration, and the flange 32*c* is secured to an end part of the transducer insert hole 33*f* of a transducer cover 33*d* having identical shape to the flange 32*c* as shown in FIG. 11.

As shown in FIGS. 11 and 12, the rigid member 33 has hollow cylindrical shape. The rigid member 33 is configured by the transducer cover 33*d* in which the ultrasonic transducer 32 is inserted and secured and an outer tube 33*e* that covers the transducer cover 33*d*, and one end of the outer tube 33*e* is connected to the flexible sheath 36. As shown in FIG. 12, although most of an inner diameter of the outer tube 33*e* contacts with an outer diameter of the transducer cover 33*d*, there is a space in which upper portion of the outer tube 33e does not touch the transducer cover 33d. A manipulator wire insert hole 33g, which is an insert hole of the manipulator wire 35, is formed at the space. Further, a portion of the cylinder at other end of the outer tube 33e is axially cut so that a coating member 33e1 having C-shaped cross section in radial direction is formed as shown in FIG. 12. An outer diameter of the outer tube 33e is formed to be smaller than the inner diameter of the channel 22b so that the outer tube 33e can be housed inside the channel 22 and the outer tube 33e can be protruded from the channel 22b.

As shown in FIGS. 10 and 11, the gripper 34 is configured by the rectangular solid grasp part 34b that has the groove part 34a at the bottom face therein, and the link body part 34c having two ear-shaped manipulator wire securing members 34c1 and 34c2 that are to be connected at a grasp member 34b side. As similar to the first embodiment, the groove part 34a of the grasp member 34b is formed to contact with the distal end treatment part 32a of the ultrasonic transducer 32 and engages thereto when the grasp member 34b is closed, in the present embodiment.

As shown in FIG. 10, the link body part 34c is provided in front of the ultrasonic transducer 32 and at a space located above the distal end treatment part 32a. The space is caused due to downward off-centering of the distal end treatment part 32a and the horn 32b of the ultrasonic transducer 32. Further, the link body part 34c is provided with the supporting pin 34d that rotatably holds the link body part 34c, and manipulator pins 34e1 and 34e2 that are used to engage each end of the two-forked manipulator wire 35 to the manipulator wire securing member 34c1 and 34c2, in the inner periphery face of the coating member 33e1.

As shown in FIG. 11, the link body part 34c is configured by lengths and widths fittable in the diameter of the outer tube 33e when the grasp member 34b is closed. Consequently, the ultrasonic treatment apparatus can be housed inside the channel 22b and the ultrasonic treatment apparatus can be protruded from the channel 22b. Further, as shown in FIG. 13, the gripper 34 can have larger stroke than the inner diameter r of the outer tube 33e when the gripper 34 rotates with respect to the supporting pin 34d that is a fulcrum.

The ultrasonic treatment apparatus of the second embodiment behaves in a way similar to the ultrasonic treatment apparatus of the first embodiment. That is to say, when the ring part 31b is pushed into the manipulator part main body 31a, the manipulator wire 35 is linked to the motion and the manipulator wire 35 is shifted toward the distal end direction of the flexible sheath 36. Then, the gripper 34 is opened since the grasp member 34b of the gripper 34 is rotated toward the H direction of the arrow with respect to the supporting pin 34d that is the fulcrum, as shown in FIG. 13. Next, the grasp member 34b is rotated toward the L direction of the arrow by shifting the ring part 31b away from the manipulator part main body 31a with respect to the supporting pin 34d that is the fulcrum. As a result, the body tissue is grasped and treatment of the body tissue can be performed since the spacing in between the distal end treatment part 32a and the grasp member 34b becomes narrower.

In the present embodiment, the distal end treatment part and the horn of the ultrasonic transducer are provided off-centered downwards with respect to the central axis of the inner periphery of the flexible sheath as well as providing the link body part at the space caused by the off-centering described above located in front of the ultrasonic transducer and above the distal end treatment part. Consequently, treatment of the body tissue inside the patient body can be performed more easily by ultrasonic vibration since the link body used to open and close the gripper is effectively housed inside the sheath and large stroke of the opening and closing of the gripper is obtained.

Figure 14:
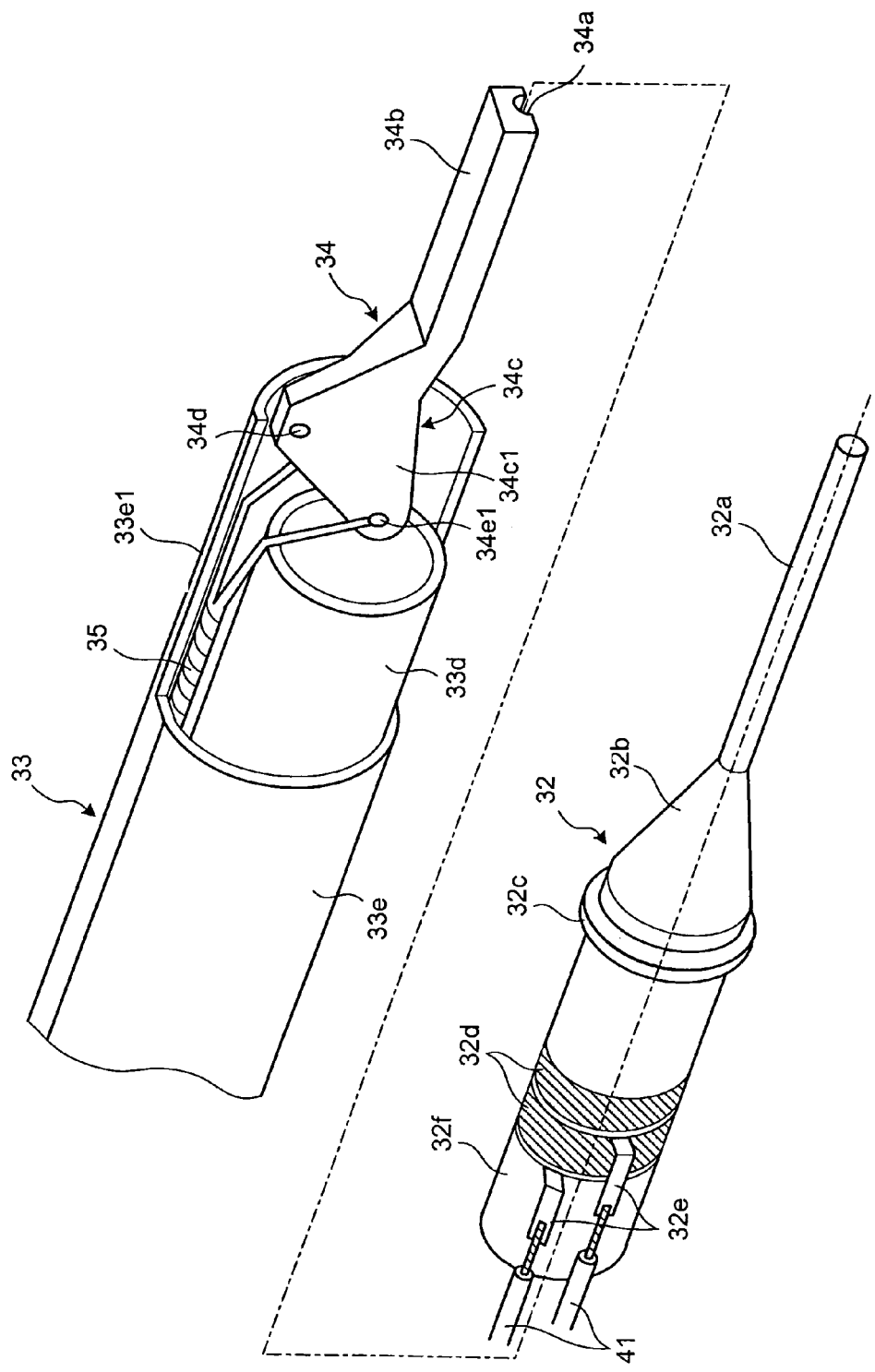
FIG. 14 is a perspective view showing a configuration of a first modification of the second embodiment of the distal end section of the ultrasonic treatment apparatus shown in FIG. 10.

FIG. 14 is a perspective view showing a configuration of a first modification of the second embodiment of the distal end section of the ultrasonic treatment apparatus shown in FIG. 10. In the first modification, the distal end treatment part 32a of the ultrasonic transducer 32 is provided at the center of the flexible sheath 36, and correspondingly, the grasp member 34b of the gripper 34 is provided at the center of the flexible sheath 36, as similar to the first embodiment.

As similar to the first embodiment, overall size of the ultrasonic treatment apparatus can be miniaturized and large stroke for opening and closing the gripper can be obtained since the link body part is provided at the space in front of the ultrasonic transducer to effectively house the link body used to open and close the grasp part inside the sheath. As a result, treatment on the body tissue inside the patient body is easily performed by ultrasonic vibration.

Figure 15:
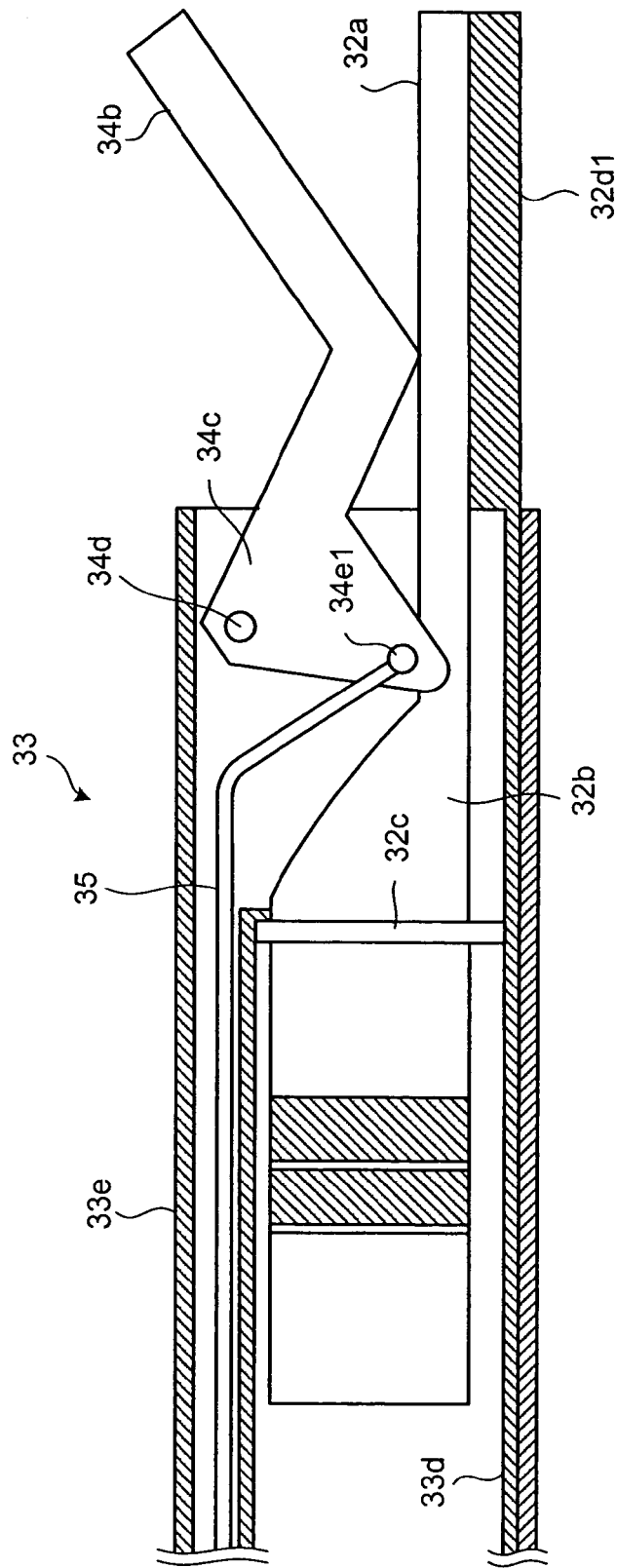
FIG. 15 is a second modification of the second embodiment of the distal end section of the ultrasonic treatment apparatus shown in FIG. 10, and is a cross-sectional side view of a distal end section of an ultrasonic treatment apparatus in which only a transducer cover and an outer tube are cut, when the distal end section of the ultrasonic treatment apparatus is opened.

FIG. 15 shows a second modification of the second embodiment of the distal end section of the ultrasonic treatment apparatus shown in FIG. 10. FIG. 15 shows a side view of the distal end section of the ultrasonic treatment apparatus in which the transducer cover and the outer tube are cut, when the distal end section of the ultrasonic treatment apparatus is opened.

In general, the distal end treatment part 32a might bend down by load thereof when the grasp member 34b of the gripper 34 is closed to grasp the body tissue in between the grasp member 34b and the distal end treatment part 32a of the ultrasonic transducer 32. The bending lowers transmission efficiency of ultrasonic vibration transmitted to the distal end treatment part 32a.

Therefore, in the second modification, the bending of the distal end treatment part 32a is prevented by providing a treatment part receiver 32d1 at the distal end section of the transducer cover 33d to support the distal end treatment part 32a from below, as shown in FIG. 15.

While having similar effect to the second embodiment, the second modification thereof can prevent the bending down of the distal end treatment part due to the load since the treatment part receiver that supports the distal end treatment part from below is provided.

The link body part 34c is supported by the supporting pin 34d at one position of the rigid member 33 in the embodiment described above. Consequently, smooth opening and closing of the gripper 34 and accurate grasping of the body tissue in between the distal end treatment part 32a and the grasp member 34b may not be performed since the entire gripper 34 wobbles while opening and closing the grasp member 34b. Therefore, an ultrasonic treatment apparatus is provided in a third embodiment to alleviate above inconvenience.

Figure 16:
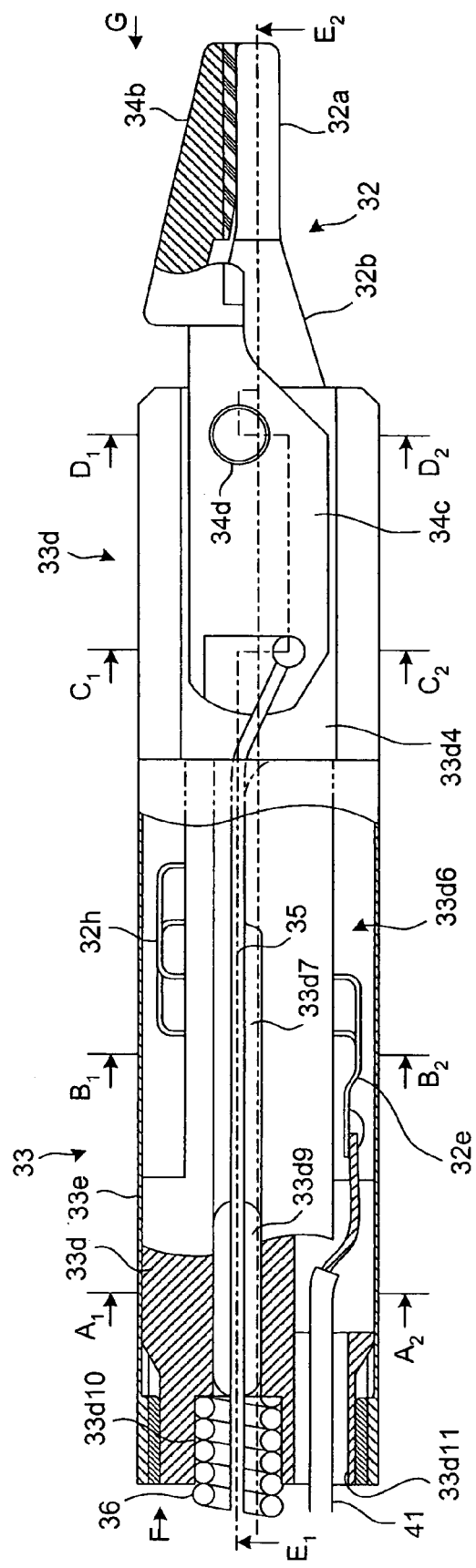
FIG. 16 is a side view showing a configuration of a distal end section of an ultrasonic treatment apparatus according to a third embodiment of the present invention, when a portion of an outer tube is truncated.
Figure 17:
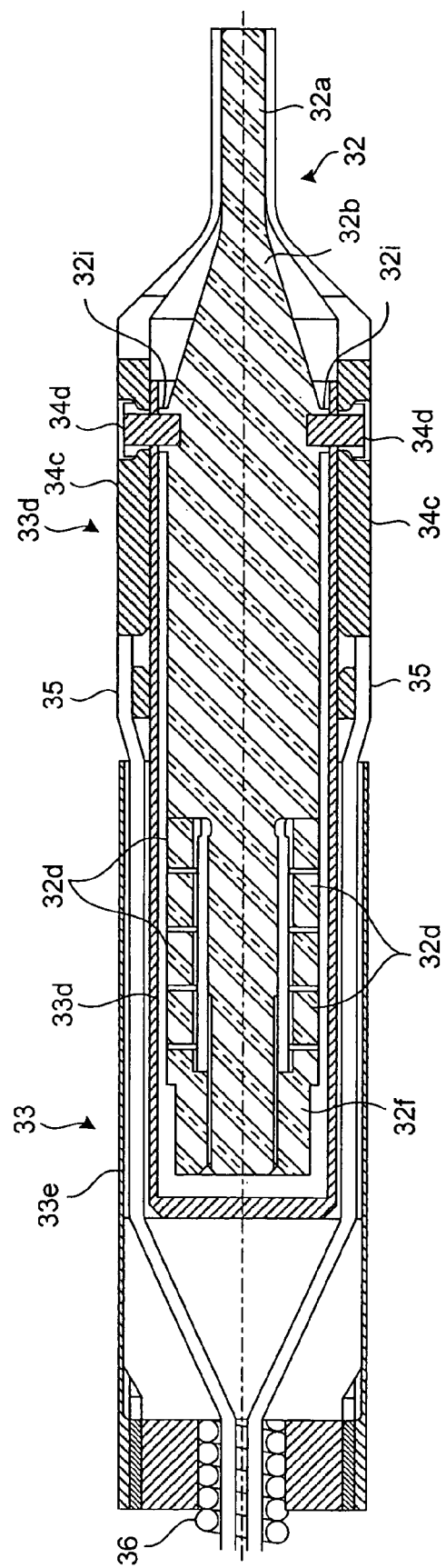
FIG. 17 is an E1-E2 cross-sectional view taken along line E1-E2 shown in FIG. 16.
Figure 18:
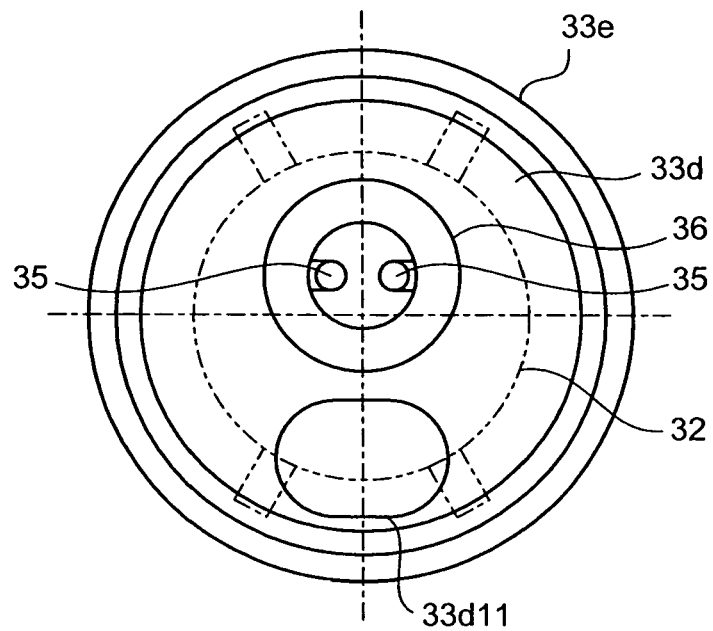
FIG. 18 is an F cross-sectional diagram of FIG. 16, seep from F arrow direction.
Figure 19:
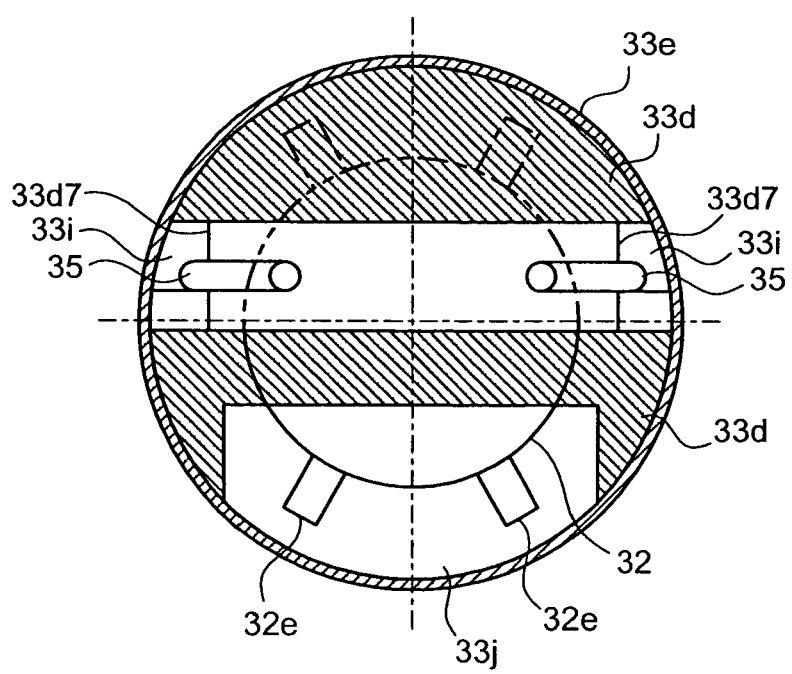
FIG. 19 is an A1-A2 cross-sectional view of FIG. 16.
Figure 20:
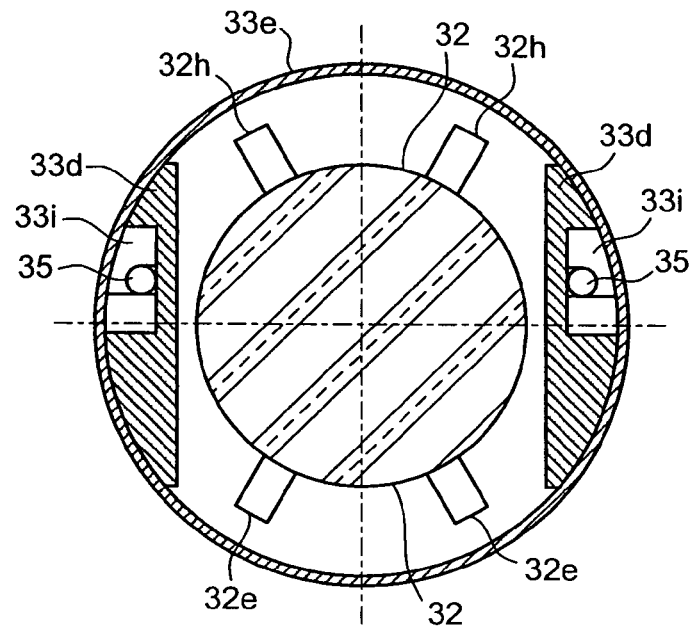
FIG. 20 is a B1-B2 cross-sectional view of FIG. 16.
Figure 21:
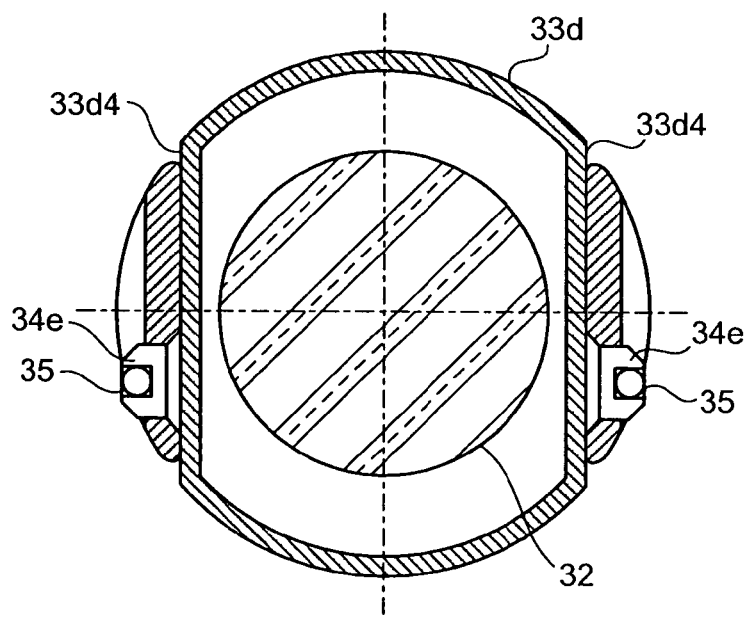
FIG. 21 is a C1-C2 cross-sectional view of FIG. 16.
Figure 22:
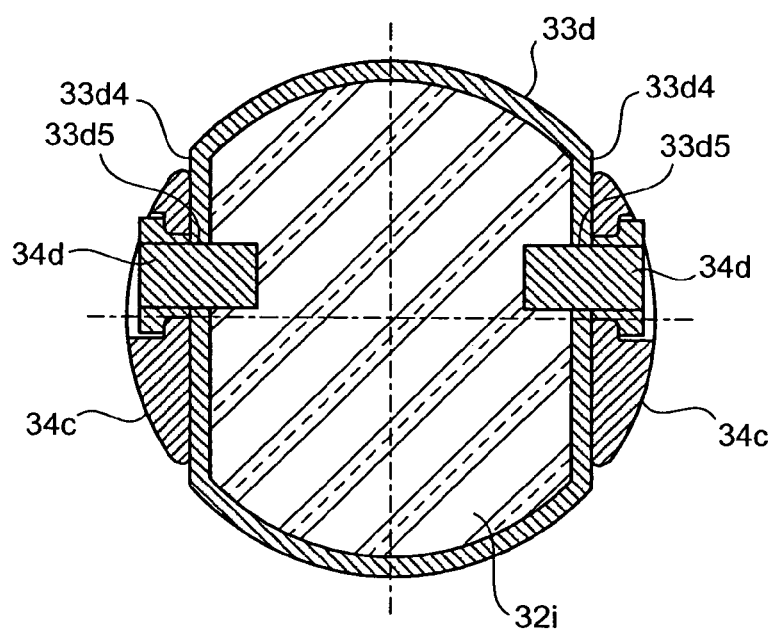
FIG. 22 is a D1-D2 cross-sectional view of FIG. 16.
Figure 23:
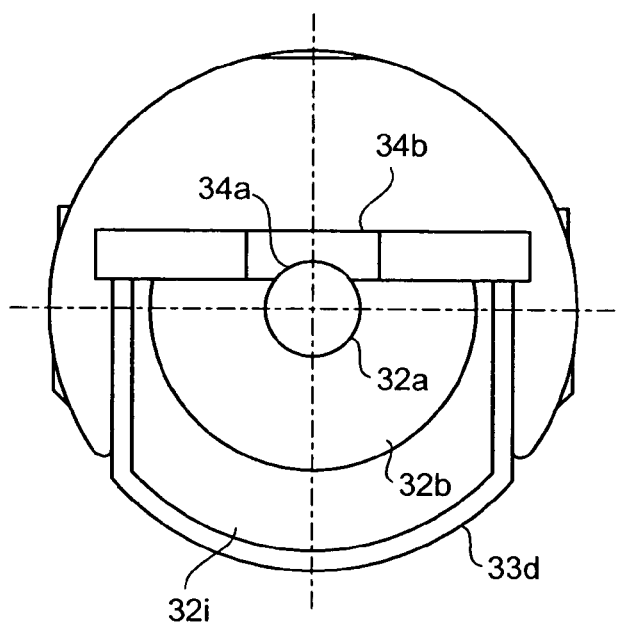
FIG. 23 is a G axial cross-sectional view of FIG. 16, seen from G arrow direction.

FIG. 16 is a side view showing a configuration of the distal end section of the ultrasonic treatment apparatus according to the third embodiment of the present invention, when a portion of an outer tube is truncated. FIG. 17 is an E1-E2 cross-sectional view taken along line E1-E2 shown in FIG. 16. FIG. 18 is an F cross-sectional diagram of FIG. 16, seen from F arrow direction. FIG. 19 is an A1-A2 cross-sectional view of FIG. 16, FIG. 20 is a B1-B2 cross-sectional view of FIG. 16, FIG. 21 is a C1-C2 cross-sectional view of FIG. 16, and FIG. 22 is a D1-D2 cross-sectional view of FIG. 16. FIG. 23 is a G cross-sectional view of FIG. 16, seen from G arrow direction. The ultrasonic transducer of the present embodiment has cylindrical shape and provided with the distal end treatment part 32a, the horn 32b, the piezoelectric element 32d, the electrode 32e, and the base 32f, as similar to the ultrasonic transducer of the second embodiment. However, the ultrasonic transducer of the present embodiment differs from those in the second embodiment by configurations that the distal end treatment part 32a is provided at the center of the flexible sheath and the flange is not provided in the present embodiment.

That is to say, a boss (flange) 32i is provided at the periphery of the ultrasonic transducer 32 and at the equilibrium position of the vibration. The boss 32i is configured to have a shape identical to the inner periphery face of the transducer cover 33d, and the boss 32i touches and is secured to the inner periphery of the transducer cover 33d. In the present embodiment, the ultrasonic transducer 32 is configured by four piezoelectric elements 32d, and each of the piezoelectric elements 32d is connected to other piezoelectric element 32d that is not adjoined thereto through a connecting member 32h. Further, the piezoelectric elements 32d are connected to the signal cable 41 through positive or negative electrode 32e.

Figure 24:
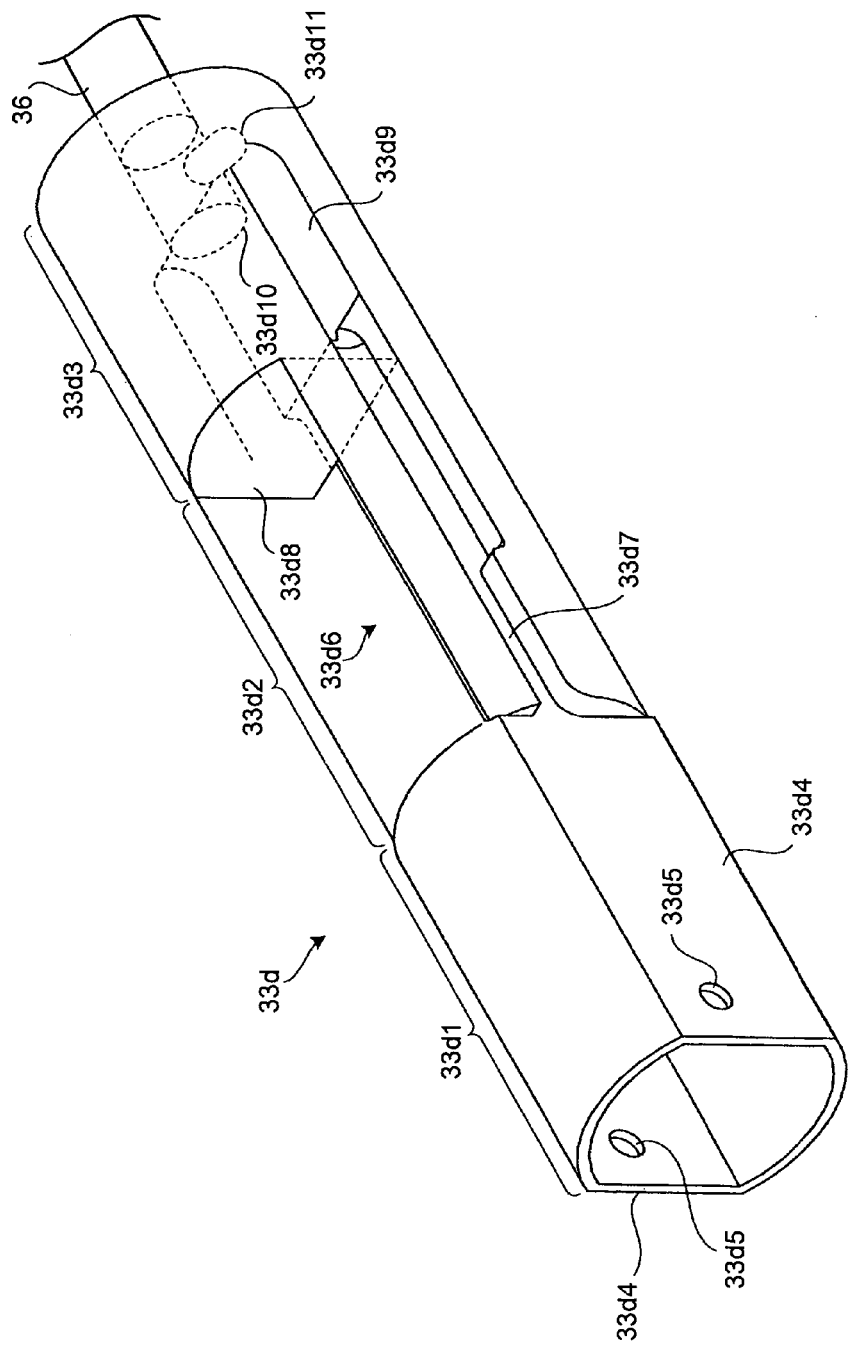
FIG. 24 is a perspective view of a transducer cover shown in FIG. 15, seen from the distal end direction.
Figure 25:
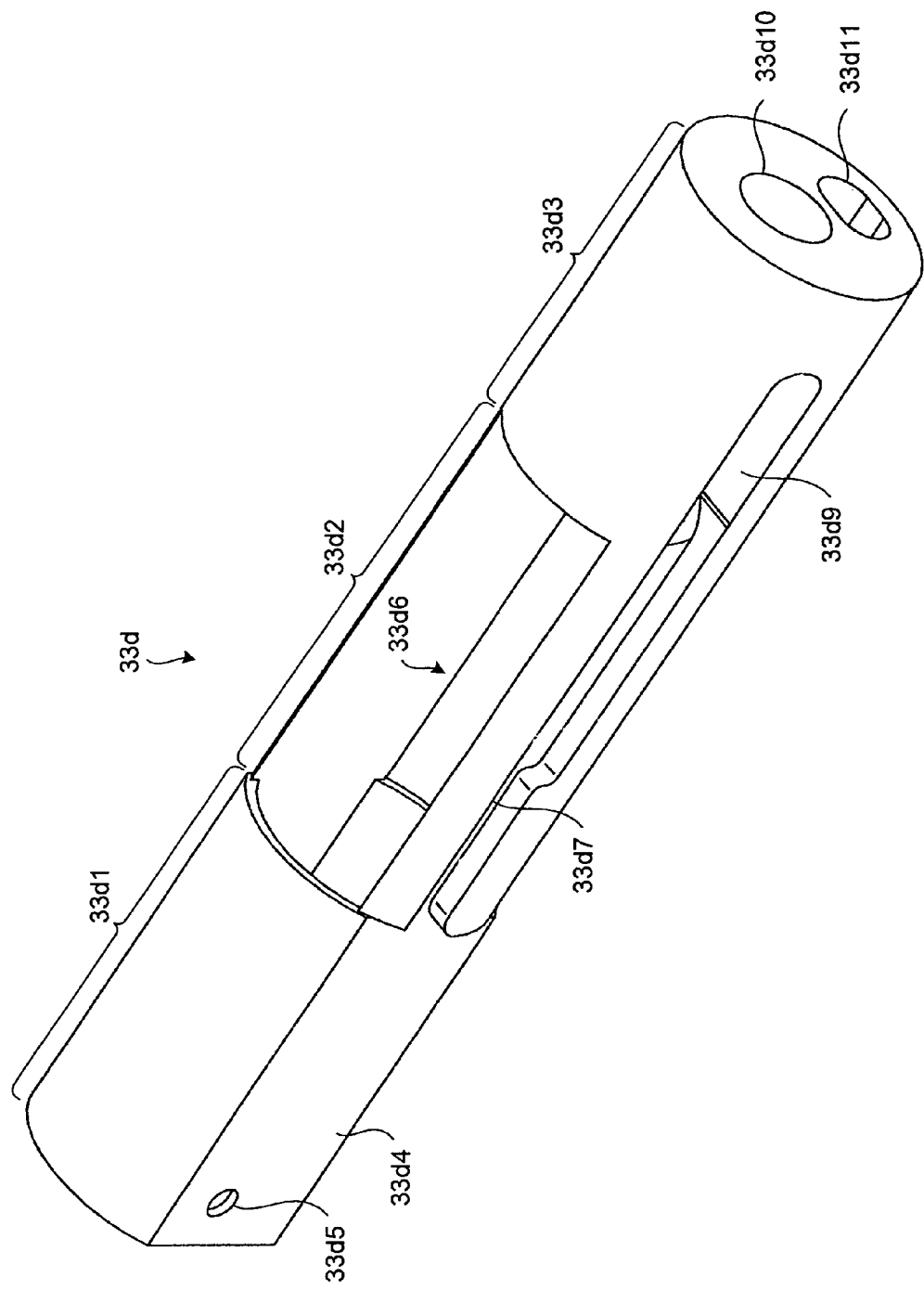
FIG. 25 is a perspective view of the transducer cover shown in FIG. 15, seen from the proximal end direction.

As similar to the second embodiment, the rigid member 33 is configured by the transducer cover 33d to which the ultrasonic transducer 32 is inserted and secured, and the outer tube 33e that is formed to cover the transducer cover 33d. Further, one end (proximal end) of the transducer cover 33d is connected to the flexible sheath 36. FIG. 24 is a perspective view of the transducer cover 33d shown in FIG. 15, seen from distal end direction, and FIG. 25 is a perspective view, seen from the proximal end direction. In FIGS. 24 and 25, the transducer cover 33d has substantially cylindrical shape, and also has a distal end part 33d1, a center part 33d2, and a proximal end part 33d3 in which each of inner shape of the parts differ from one another.

The distal end part 33d1 has hollow shape enabling the ultrasonic transducer 32 to be housed therein, and both side faces are chamfered to form two attaching faces 33d4. Two engaging holes 33d5 opposing to each other are formed on the attaching faces 33d4 to engage with a pair of supporting pins.

The center part 33d2 is hollowed out in vertical direction to form a space 33d6, and a U-shaped cross section of a groove 33d7 is formed in longitudinal direction. As shown in FIGS. 16 and 20, the distal end section (the distal end part 33d1 side) of the groove 33d7 is formed in R shape. If the distal end of the groove 33d7 would be formed with an edge of 90 degrees in angle, there would be a possibility that the manipulator wire 35 might be caught at the entrance. Hence, the edge is formed to have R shape to prevent the problem described above. Other than forming the edge of the distal end section to R shape, the edge can be formed to have, for example, more than or equal to 100 degrees in inclination in order to prevent the manipulator wire 35 to be caught. A distal end side in longitudinal direction of the center part 33d2 is communicatively connected to the hollow section of the distal end part 33d1 so that the ultrasonic transducer 32 can be housed therein, and a diaphragm 33d8 is formed at a proximal end side of the center part 33d2.

A side hole 33d9 that penetrates horizontally is formed at the proximal end part 33d3, and an end part in longitudinal direction of the side hole 33d9 is formed to be R-shaped as well as the side hole 33d9 is communicatively connected to the groove 33d7 of the center part 33d2. A connecting hole 33d10 that communicatively connected to the connected flexible sheath 36 is formed at a proximal end part of the side hole 33d9. Consequently, the manipulator wire 35 that protrudes from the flexible sheath 36 runs through the connecting hole 33d10 and spread in radial direction of the transducer cover 33d at the side hole 33d9. Then, the manipulator wires 35 run through the grooves 33d7 of the center part 33d2 to reach the attaching faces 33d4 of the distal end part 33d1. A communicative connecting hole 33d11 that communicatively connected to the space 33d6 of the center part 33d2 is formed below the connecting hole 33d10, and the signal cable 41 from the driving unit 4 is inserted into the communicatively connecting hole 33d11 so that the signal cable 41 can reach the space 33d6 of the center part 33d2. Substantially half of the transducer cover 33d is inserted into the outer tube 33e, and secured therein by, for example, a screw.

As shown in FIGS. 19 and 20, although most of the inner diameter of the outer tube 33e is in contact with the outer diameter of the transducer cover 33d near A1-A2 cross section, spaces are formed by grooves 33d7 at portions located left and right of the outer tube 33e. Here, insert holes 33i of the manipulator wires are formed as the spaces. Furthermore, an space not in contact with the transducer cover 33d, which is an insert hole 33j of the signal cable 41, is formed at lower part of the outer tube 33e. Further, only left and right parts of the inner diameter of the outer tube 33e are in contact with the outer periphery of the transducer cover 33d near B1-B2 cross section, as shown in FIG. 20.

As shown in FIGS. 16, 21, 22, and 23, the gripper 34 has axially slender groove part 34a at the bottom face, and the gripper 34 is configured by the grasp member 34b that has triangular shape on the side thereof and the link body part 34c that is provided on a backside of the grasp member 34b. Further, the gripper 34 is formed so that the groove 34a contacts the distal end treatment part 32a of the ultrasonic transducer 32 and engages thereto when the grasp member 34b is closed.

As shown in FIGS. 21 and 22, two of the cross-sectional shapes of the link body parts 34c are formed in D shapes that cover the outer periphery of the attaching face 33d4 of the transducer cover 33d. The link body part 34c has the supporting pins 34d that engage to engaging holes 33d5 provided on the attaching face 33d4. Further, the link body part 34c has the manipulator pins 34e by which each end of the manipulator wire 35 is engaged to the link body part 34c. Here, the link body part 34c is provided with respect to the supporting pins 34d at two points so that the link body part 34c rotates along the attaching face 33d4. The supporting pins 34d, which are the fulcrums for opening and closing of the grasp member 34b, is preferably provided above the manipulator pins 34e, which are points of action. Further, the supporting pins 34e are preferably arranged above the central axis of the transducer cover 33d in longitudinal direction, and the manipulator pins 34e are preferably arranged below the central axis thereof. Consequently, grasp force necessary to accurately grasp the body tissue is obtained when the manipulator wire 35 is pulled toward the flexible sheath 36 to close the gripper 34. Further, the gripper 34 rotates with respect to the fulcrum, which is the supporting pin 34d, when the manipulator wire 35 is pushed away from the flexible sheath 36. Consequently, the gripper 34 opens easily, and the body tissue can be released easily.

As shown in FIGS. 22 and 24, the boss 32i that has a function of the flange of the ultrasonic transducer 32 is provided at the positions of two engaging holes 33d5 of the distal end part 33d1, and the bosses 32i are secured to the distal end part 33d1 of the transducer cover 33d by fitting with the two supporting pins 34d. The supporting pins 34d has a function of supporting means to rotatably supports the gripper 34, and a function of securing means to secure the ultrasonic transducer 32 to the transducer cover 33d. Consequently, the ultrasonic transducer can be secured without using a flange or a securing screw.

Figure 26:
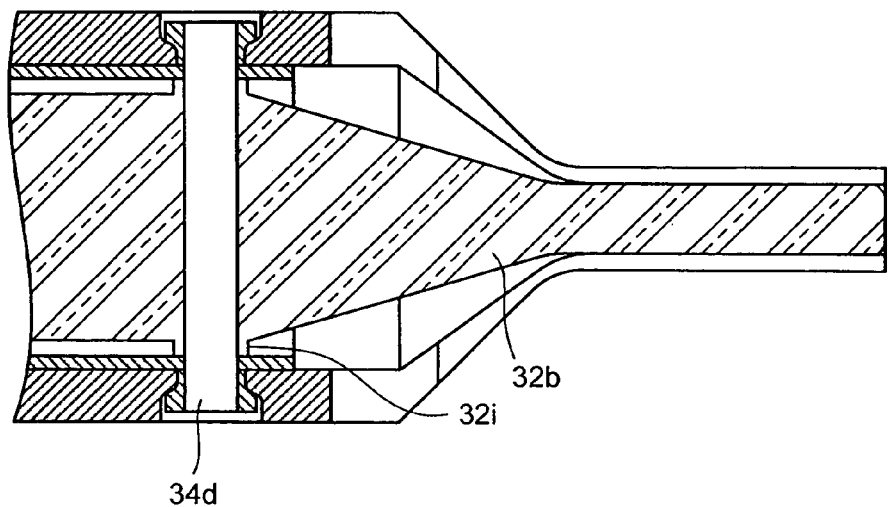
FIG. 26 is a cross-sectional view showing a first modification of the E1-E2 cross section shown in FIG. 17.
Figure 27:
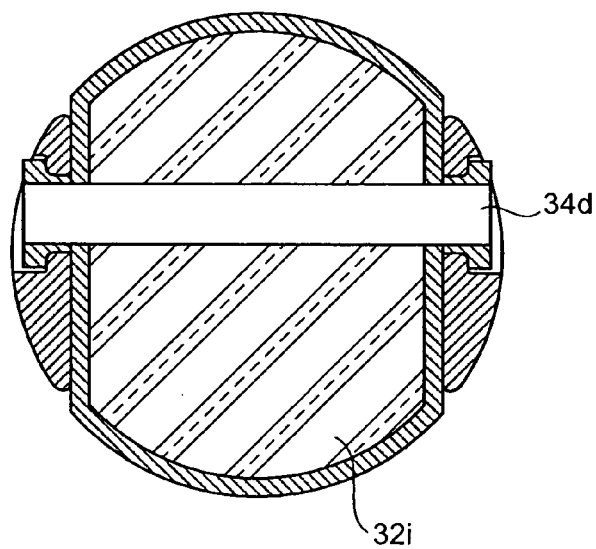
FIG. 27 is a D1-D2 cross-sectional view in the modification shown in FIG. 26.
Figure 28:
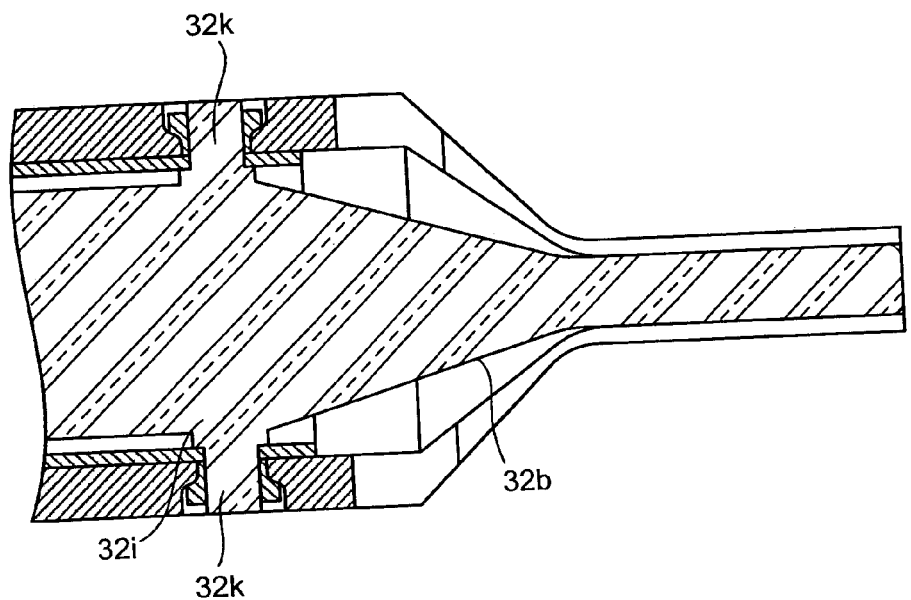
FIG. 28 is a cross-sectional view showing a second modification of the E1-E2 cross section shown in FIG. 17.
Figure 29:
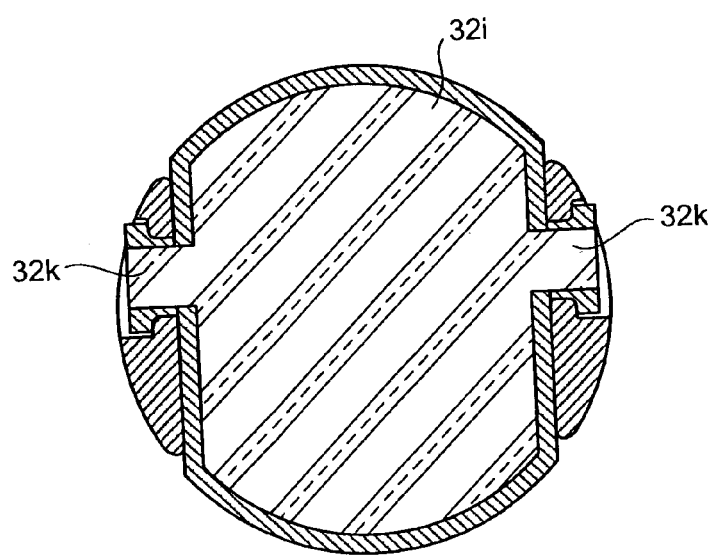
FIG. 29 is a D1-D2 cross-sectional view in the modification shown in FIG. 28.

A configuration of the supporting pin 34d according to the present invention is not limited to the above embodiments, and the supporting pin 34d can penetrate through the flange 32i as shown in FIGS. 26 and 27. Further, a small boss 32k can be provided on the flange 32i to replace the supporting pin 34d, as shown in FIGS. 28 and 29.

The outer diameter of the outer tube 33e is set to be smaller than the inner diameter of the cannel 22b of the ultrasonic treatment apparatus. Combined diameter of the outer diameter of the transducer cover 33d in horizontal direction and the thickness of the link body parts 34c is equal to the outer diameter of the outer tube 33e, and substantially equal to the outer diameter of the transducer cover 33d in longitudinal direction as shown in FIG. 22. Consequently, the outer tube 33e and the transducer cover 33d can be housed inside the channel 22b of the ultrasonic treatment apparatus, and the outer tube 33e and the transducer cover 33d can be protruded from the channel 22b. As similar to the ultrasonic treatment apparatus of the first and the second embodiments, the ultrasonic treatment apparatus of the third embodiment can accurately grasp the body tissue to perform treatment.

Consequently, the ultrasonic treatment apparatus of the present embodiment can obtain the similar effect to the ultrasonic treatment apparatus of the first and the second embodiments. Further, the transducer cover rotatably supports the gripper of the ultrasonic treatment apparatus of the present embodiment by the pair of fulcrums, which is made by the two supporting pins; therefore, the entire gripper does not wobble when the grasp member is opened and closed. As a result, smooth opening and closing of the grasp member and accurate grasping of the body tissue in between the distal end treatment part and the grasp member can be performed.

Further, the rigid member of the distal end of the ultrasonic treatment apparatus has dual structure configured by the outer tube and the transducer cover, and the groove is provided to house the manipulator wire in between the outer tube and the transducer cover. Consequently, there is less exposure of the manipulator wire, and motion of the manipulator wire is confined; therefore, the opening and closing of the gripper can be accurately performed since the manipulator wire does not bend even if the rigid portion of the ultrasonic transducer becomes longer.

Further, the hole provided on the transducer cover to be used for the manipulator wire and the hole to be used for the signal cable are provided so that the passages of the manipulator wire differs from the passage of the signal cable to prevent the interference therebetween, in the present embodiment. Further, water tightness of the ultrasonic transducer can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
a sheath that includes an opening at a distal end thereof, and is configured to be inserted into a body from the distal end;
a rigid member that is in a substantially cylindrical shape and attached to the distal end of the sheath;
an ultrasonic transducer that is provided in a distal end of the rigid member, and generates ultrasonic vibration;
an ultrasonic transmission member that includes a treatment part protruding from the rigid member, and transmits the ultrasonic vibration generated by the ultrasonic transducer to the treatment part;
a gripper that is rotatably attached to the rigid member, and grasps a part to be treated with the treatment part;
a wire that is inserted in the sheath, a first end of the wire being connected to the gripper; and
a manipulator part that is connected to a second end of the wire to manipulate the gripper to an open position and a closed position with respect to the treatment part, wherein
the rigid member includes an ultrasonic transducer holder having a truncated circular cross-section to hold the ultrasonic transducer therein, and
a connecting part of the gripper and the wire is located in a space adjacent of the ultrasonic transducer holder.

2. The ultrasonic treatment apparatus according to claim 1, wherein
the gripper includes a gripping matter that is rotatably attached to a side of the rigid member, and protrudes from the rigid member to grasp the part to be treated with the treatment part, and
the first end of the wire is connected to the gripper outside the rigid member.

3. The ultrasonic treatment apparatus according to claim 1, wherein the treatment part is provided at an eccentric position with respect to an axis passing through a center of an inner periphery of the sheath.

4. The ultrasonic treatment apparatus according to claim 1, further comprising a supporting member that rotatably supports the gripper with respect to the rigid member.

5. The ultrasonic treatment apparatus according to claim 4, wherein
the gripper includes a securing member that extends from a position supported by the supporting member in a direction toward an axis passing through a center inside the rigid member, and
the first end of the wire is connected to the securing member at a position other than the position supported by the supporting member.

6. The ultrasonic treatment apparatus according to claim 1, further comprising a supporting member that rotatably supports the gripper with respect to the rigid member, wherein
the treatment part is provided at an eccentric position with respect to an axis passing through a center of an inner periphery of the sheath, and
the supporting member rotatably supports the gripper with respect to the rigid member on a side opposite the eccentric position.

7. The ultrasonic treatment apparatus according to claim 1, wherein the rigid member includes
a transducer cover that covers the ultrasonic transducer, and an outer tube that covers the transducer cover.

8. The ultrasonic treatment apparatus according to claim 7, wherein the transducer cover includes
a communicative connection hole that is communicatively connected to the ultrasonic transducer holder,
a groove that is formed in a longitudinal direction of the transducer cover and has a U-shaped cross section to dispose the wire,
a side hole that is communicatively connected to the groove, and
a connecting hole for wiring.

9. The ultrasonic treatment apparatus according to claim 1, wherein the sheath is flexible.

10. An ultrasonic treatment apparatus comprising:

a sheath that includes an opening at a distal end thereof, and is configured to be inserted into a body from the distal end;

a rigid member that has a cylindrical portion and is attached to the distal end of the sheath;

an ultrasonic transducer that is provided in the rigid member, and generates ultrasonic vibration;

an ultrasonic transmission member that includes a treatment part protruding from the rigid member, and transmits the ultrasonic vibration generated by the ultrasonic transducer to the treatment part;

a gripper that is rotatably attached to the rigid member, and grasps a part to be treated with the treatment part;

a wire that is inserted in the sheath, a first end of the wire being connected to the gripper; and a manipulator part that is connected to a second end of the wire to manipulate the gripper to an open position and a closed position with respect to the treatment part;

wherein the rigid member includes, in part of a side thereof, a plane surface parallel to a direction in which the sheath is inserted into and removed from the patient to be treated, the gripper is rotatably attached to the plane surface of the rigid member, and the first end of the wire is connected to the gripper at a pivot having an axis of rotation perpendicular to the plane surface.

* * * * *